(12) United States Patent
Soykan et al.

(10) Patent No.: US 9,289,165 B2
(45) Date of Patent: Mar. 22, 2016

(54) ION IMBALANCE DETECTOR

(71) Applicant: Medtronic, Inc., Minneapolis, MN (US)

(72) Inventors: Orhan Soykan, Shoreview, MN (US); Timothy H. Robinson, Savage, MN (US); James K. Carney, Eden Prairie, MN (US); Tara L. Nahey, Minneapolis, MN (US); Cygni Chan, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/514,829

(22) Filed: Oct. 15, 2014

(65) Prior Publication Data
US 2015/0032023 A1      Jan. 29, 2015

Related U.S. Application Data

(62) Division of application No. 11/349,540, filed on Feb. 7, 2006, now Pat. No. 8,903,492.

(60) Provisional application No. 60/650,497, filed on Feb. 7, 2005.

(51) Int. Cl.
*A61N 1/36* (2006.01)
*A61B 5/145* (2006.01)
(Continued)

(52) U.S. Cl.
CPC ........... *A61B 5/14546* (2013.01); *A61B 5/1107* (2013.01); *A61B 5/1451* (2013.01); *A61B 5/1473* (2013.01); *A61B 5/14542* (2013.01); *A61B 5/4519* (2013.01); *A61B 5/7278* (2013.01); *A61N 1/36135* (2013.01); *A61N 1/36557* (2013.01); *A61B 5/053* (2013.01);
(Continued)

(58) Field of Classification Search
CPC .................................................. A61N 1/36557
See application file for complete search history.

(56) References Cited

U.S. PATENT DOCUMENTS 3,608,729 A   9/1971   Haselden
3,669,878 A   6/1972   Marantz
(Continued)

FOREIGN PATENT DOCUMENTS

EP   266795 A2    11/1987
EP   1364666 A1   11/2003
(Continued)

OTHER PUBLICATIONS

U.S. Appl. No. 13/837,287, filed Mar. 15, 2013, Pudil.
(Continued)

*Primary Examiner* — Eric D. Bertram
(74) *Attorney, Agent, or Firm* — Hahn & Voight PLLC; Roger C. Hahn; Kenneth J. Collier

(57) ABSTRACT

In general, the invention is directed to methods and devices for determining an ion concentration in the extracellular fluid of a patient. As examples, the ion may be one or more of potassium, sodium, chloride, or calcium. A system includes an electrode deployed in or near a tissue, such as a skeletal muscle, of the patient. A pulse generator supplies one or more stimulations to the tissue, and a sensor, such as an accelerometer, detects the response of the tissue to the stimulations. A processor determines a concentration of ions in the extracellular fluid as a function of the response. The system may detect an ion imbalance based upon the determined concentration of ions.

19 Claims, 13 Drawing Sheets

(51) Int. Cl.
  *A61B 5/11* (2006.01)
  *A61B 5/1473* (2006.01)
  *A61B 5/00* (2006.01)
  *A61N 1/365* (2006.01)
  *A61B 5/053* (2006.01)
  *A61M 5/142* (2006.01)
  *A61M 5/172* (2006.01)

(52) U.S. Cl.
  CPC ......... *A61B5/686* (2013.01); *A61B 2562/0219* (2013.01); *A61M 5/14276* (2013.01); *A61M 5/1723* (2013.01); *A61N 1/36167* (2013.01)

(56) References Cited

U.S. PATENT DOCUMENTS

| | | | |
|---|---|---|---|
| 3,669,880 | A | 6/1972 | Marantz |
| 3,850,835 | A | 11/1974 | Marantz |
| 3,884,808 | A | 5/1975 | Scott |
| 3,989,622 | A | 11/1976 | Marantz |
| 4,060,485 | A | 11/1977 | Eaton |
| 4,371,385 | A | 2/1983 | Johnson |
| 4,374,382 | A | 2/1983 | Markowitz |
| 4,381,999 | A | 5/1983 | Boucher |
| 4,460,555 | A | 7/1984 | Thompson |
| 4,556,063 | A | 12/1985 | Thompson |
| 4,562,751 | A | 1/1986 | Nason |
| 4,581,141 | A | 4/1986 | Ash |
| 4,650,587 | A | 3/1987 | Polak |
| 4,678,408 | A | 7/1987 | Mason |
| 4,685,903 | A | 8/1987 | Cable |
| 4,750,494 | A * | 6/1988 | King .............................. 607/14 |
| 4,826,663 | A | 5/1989 | Alberti |
| 4,828,693 | A | 5/1989 | Lindsay |
| 5,080,653 | A | 1/1992 | Voss |
| 5,092,886 | A | 3/1992 | Dobos-Hardy |
| 5,097,122 | A | 3/1992 | Coiman |
| 5,127,404 | A | 7/1992 | Wyborny |
| 5,284,470 | A | 2/1994 | Beltz |
| 5,302,288 | A | 4/1994 | Meidl |
| 5,305,745 | A | 4/1994 | Zacouto |
| 5,318,750 | A | 6/1994 | Lascombes |
| 5,468,388 | A | 11/1995 | Goddard |
| 5,683,432 | A | 11/1997 | Goedeke |
| 5,762,782 | A | 6/1998 | Kenley |
| 5,944,684 | A | 8/1999 | Roberts |
| 6,048,732 | A | 4/2000 | Anslyn |
| 6,052,622 | A | 4/2000 | Holmstrom |
| 6,058,331 | A | 5/2000 | King |
| 6,230,059 | B1 | 5/2001 | Duffin |
| 6,248,093 | B1 | 6/2001 | Moberg |
| 6,254,567 | B1 | 7/2001 | Treu |
| 6,321,101 | B1 | 11/2001 | Holmstrom |
| 6,362,591 | B1 | 3/2002 | Moberg |
| 6,363,279 | B1 | 3/2002 | Ben-Haim |
| 6,554,798 | B1 | 4/2003 | Mann |
| 6,555,986 | B2 | 4/2003 | Moberg |
| 6,589,229 | B1 | 7/2003 | Connelly |
| 6,602,399 | B1 | 8/2003 | Fromherz |
| 6,627,164 | B1 | 9/2003 | Wong |
| 6,676,608 | B1 | 1/2004 | Keren |
| 6,711,439 | B1 | 3/2004 | Bradley |
| 6,818,196 | B2 | 11/2004 | Wong |
| 6,878,283 | B2 | 4/2005 | Thompson |
| 6,960,179 | B2 | 11/2005 | Gura |
| 7,077,819 | B1 | 7/2006 | Goldau |
| 7,208,092 | B2 | 4/2007 | Micheli |
| 7,276,042 | B2 | 10/2007 | Polaschegg |
| 7,566,432 | B2 | 7/2009 | Wong |
| 7,575,564 | B2 | 8/2009 | Childers |
| 7,674,231 | B2 | 3/2010 | McCombie |
| 7,704,361 | B2 | 4/2010 | Garde |
| 7,736,507 | B2 | 6/2010 | Wong |
| 7,754,852 | B2 | 7/2010 | Burnett |
| 7,756,572 | B1 | 7/2010 | Fard |
| 7,776,210 | B2 | 8/2010 | Rosenbaum |
| 7,794,141 | B2 | 9/2010 | Perry |
| 7,850,635 | B2 | 12/2010 | Polaschegg |
| 7,867,214 | B2 | 1/2011 | Childers |
| 7,922,686 | B2 | 4/2011 | Childers |
| 7,922,911 | B2 | 4/2011 | Micheli |
| 7,947,179 | B2 | 5/2011 | Rosenbaum |
| 7,967,022 | B2 | 6/2011 | Grant |
| 7,981,082 | B2 | 7/2011 | Wang |
| 8,034,161 | B2 | 10/2011 | Gura |
| 8,070,709 | B2 | 12/2011 | Childers |
| 8,096,969 | B2 | 1/2012 | Roberts |
| 8,183,046 | B2 | 5/2012 | Lu |
| 8,187,250 | B2 | 5/2012 | Roberts |
| 8,246,826 | B2 | 8/2012 | Wilt |
| 8,273,049 | B2 | 9/2012 | Demers |
| 8,292,594 | B2 | 10/2012 | Tracey |
| 8,313,642 | B2 | 11/2012 | Yu |
| 8,317,492 | B2 | 11/2012 | Demers |
| 8,357,113 | B2 | 1/2013 | Childers |
| 8,366,316 | B2 | 2/2013 | Kamen |
| 8,366,655 | B2 | 2/2013 | Kamen |
| 8,409,441 | B2 | 4/2013 | Wilt |
| 8,499,780 | B2 | 8/2013 | Wilt |
| 8,518,260 | B2 | 8/2013 | Raimann |
| 8,535,525 | B2 | 9/2013 | Heyes |
| 8,580,112 | B2 | 11/2013 | Updyke |
| 8,597,227 | B2 | 12/2013 | Childers |
| 8,696,626 | B2 | 4/2014 | Kirsch |
| 8,903,492 | B2 | 12/2014 | Soykan et al. |
| 2002/0042561 | A1 | 4/2002 | Schulman |
| 2002/0112609 | A1 | 8/2002 | Wong |
| 2003/0080059 | A1 | 5/2003 | Peterson |
| 2003/0097086 | A1 | 5/2003 | Gura |
| 2003/0105435 | A1 | 6/2003 | Taylor |
| 2003/0114787 | A1 | 6/2003 | Gura |
| 2004/0019312 | A1 | 1/2004 | Childers |
| 2004/0099593 | A1 | 5/2004 | DePaolis |
| 2004/0147900 | A1 | 7/2004 | Polaschegg |
| 2004/0215090 | A1 | 10/2004 | Erkkila |
| 2005/0065760 | A1 | 3/2005 | Murtfeldt |
| 2005/0113796 | A1 | 5/2005 | Taylor |
| 2005/0126961 | A1 | 6/2005 | Bissler |
| 2005/0126998 | A1 | 6/2005 | Childers |
| 2005/0150832 | A1 | 7/2005 | Tsukamoto |
| 2005/0234381 | A1 | 10/2005 | Niemetz |
| 2005/0236330 | A1 | 10/2005 | Nier |
| 2005/0274658 | A1 | 12/2005 | Rosenbaum |
| 2006/0025661 | A1 | 2/2006 | Sweeney |
| 2006/0195064 | A1 | 8/2006 | Plahey |
| 2006/0217771 | A1 | 9/2006 | Soykan |
| 2006/0226079 | A1 | 10/2006 | Mori |
| 2006/0241709 | A1 | 10/2006 | Soykan |
| 2006/0264894 | A1 | 11/2006 | Moberg |
| 2007/0007208 | A1 | 1/2007 | Brugger |
| 2007/0066928 | A1 | 3/2007 | Lannoy |
| 2007/0138011 | A1 | 6/2007 | Hofmann |
| 2007/0175827 | A1 | 8/2007 | Wariar |
| 2007/0179431 | A1 | 8/2007 | Roberts |
| 2007/0215545 | A1 | 9/2007 | Bissler |
| 2007/0255250 | A1 | 11/2007 | Moberg |
| 2008/0006570 | A1 | 1/2008 | Gura |
| 2008/0021337 | A1 | 1/2008 | Li |
| 2008/0053905 | A9 | 3/2008 | Brugger |
| 2008/0067132 | A1 | 3/2008 | Ross |
| 2008/0215247 | A1 | 9/2008 | Tonelli |
| 2009/0020471 | A1 | 1/2009 | Tsukamoto |
| 2009/0101577 | A1 | 4/2009 | Fulkerson |
| 2009/0127193 | A1 | 5/2009 | Updyke |
| 2009/0275849 | A1 | 11/2009 | Stewart |
| 2009/0275883 | A1 | 11/2009 | Chapman |
| 2009/0281484 | A1 | 11/2009 | Childers |
| 2009/0282980 | A1 | 11/2009 | Gura |
| 2010/0004588 | A1 | 1/2010 | Yeh |
| 2010/0010429 | A1 | 1/2010 | Childers |
| 2010/0078381 | A1 | 4/2010 | Merchant |
| 2010/0078387 | A1 | 4/2010 | Wong |
| 2010/0084330 | A1 | 4/2010 | Wong |
| 2010/0094158 | A1 | 4/2010 | Solem |

(56) References Cited

U.S. PATENT DOCUMENTS

| | | |
|---|---|---|
| 2010/0114012 A1 | 5/2010 | Sandford |
| 2010/0137693 A1 | 6/2010 | Porras |
| 2010/0168546 A1 | 7/2010 | Kamath |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2011/0017665 A1 | 1/2011 | Updyke |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0184340 A1 | 7/2011 | Tan |
| 2011/0272337 A1 | 11/2011 | Palmer |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0199998 A1 | 8/2013 | Kelly |
| 2013/0213890 A1 | 8/2013 | Kelly |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0220699 A1 | 8/2014 | Pudil |

FOREIGN PATENT DOCUMENTS

| | | |
|---|---|---|
| EP | 0906768 B1 | 2/2004 |
| EP | 1450879 | 10/2008 |
| EP | 1592494 B1 | 6/2009 |
| EP | 2100553 A1 | 9/2009 |
| EP | 2575827 A2 | 12/2010 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 2701596 | 3/2014 |
| JP | 5099464 | 10/2012 |
| WO | 9937342 | 7/1999 |
| WO | 0057935 | 10/2000 |
| WO | 0170307 A1 | 9/2001 |
| WO | 0185295 A2 | 9/2001 |
| WO | 0066197 A1 | 11/2001 |
| WO | 03043680 | 5/2003 |
| WO | 2003043677 A2 | 5/2003 |
| WO | 03051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2005123230 A2 | 12/2005 |
| WO | 2007089855 A2 | 8/2007 |
| WO | 2009026603 | 3/2009 |
| WO | 2009026603 A1 | 3/2009 |
| WO | 2009157877 | 12/2009 |
| WO | 2009157878 | 12/2009 |
| WO | 2010028860 | 3/2010 |
| WO | WO2010028860 A1 | 3/2010 |
| WO | 2011025705 A1 | 3/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013028809 A3 | 2/2013 |
| WO | 2013103607 A1 | 7/2013 |
| WO | 2013103906 | 7/2013 |
| WO | 2013114063 A | 8/2013 |
| WO | 2013121162 A1 | 8/2013 |
| WO | 2014066254 | 5/2014 |
| WO | 2014066255 | 5/2014 |
| WO | 2014077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Leifer, I., et al., A Study on the Temperature Variation of Rise Velocity for Large Clean Bubbles, J. Atmospheric & Oceanic Tech., vol. 17, pp. 1392-1402.

Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.

Talaia, MAR, Terminal Velocity of a Bubble Rise in a Liquid Column, Talaia, World Acad. of Sci., Engineering & Tech., vol. 28, pp. 264-268.

The FHN Trial Group. In-Center. Hemodialysis Six Times per Week versus Three Times per Week, New England Journal of Medicine, 2010.

U.S. Appl. No. 13/757,693, filed Feb. 1, 2013.

PCT/US2014/014357 International Search Report and Written Opinion.

U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/757,792, filed Feb. 2, 2013.
U.S. Appl. No. 13/837,287, filed Mar. 15, 2013.
U.S. Appl. No. 13/757,794, filed Feb. 2, 2013.

Bleyer, et. al., Sudden and cardiac death rates in hemodialysis patients, Kidney International, 1999, 1553-1559 : 55.

MacLean, et, al., Effects of hindlimb contraction on pressor and muscle interstitial metabolite responses in the cat, J. App. Physiol., 1998, 1583-1592, 85 (4).

Overgaard, et. al., Activity-induced recovery of excitability in K+-depressed rat soieus muscle, Am. J. P.

Overgaard. et. al., Relations between excitability and contractility in rate soleus'muscle: role of the Na+—K+ pump and NA+-K—S gradients. Journal of Physiology, 1999, 215-225, 518(1).

PCT/US2012/034330, International Search Report, Aug. 28, 2012.
PCT/US2012/034332, International Search Report, Jul. 5, 2012.

Roberts M, The regenerative dialysis (REDY) sorbent system. Nephrology, 1998, 275-278:4.

Ronco, et. al., "Cardiorenal Syndrome", J. Am. Coll. Cardiol., 2008, 1527-1539 : 52.

Siegenthalar, et. al., Pulmonary fluid status monitoring with intrathoracic impedance, Journal of Cli.

U.S. Appl. No. 60/650,497.
U.S. Appl. No. 61/480,544.

(56) References Cited

OTHER PUBLICATIONS

Wang, Fundamentals of intrathoracic impedance monitoring in heart failure, Am. J. Cardiology, 2007, 3G-10G : Suppl.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Wang, Fundamentals of intrathoracic impedance monitoring in heart failure, Am. J. Cardiology, 2007, 3G-310: Suppl.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, Aug. 13, 2013.
PCT/US/2012/034329, International Search Report, Dec. 3, 2012.
PCT/US2012/034331, International Search Report, Jul. 9, 2012.
PCT/US2012/034334, International Search Report, Jul. 6, 2012.
PCT/US2012/034335, International Search Report, Sep. 5, 2012.
Redfield, et. al, Restoration of renal response to atria.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Coast, et al. 1990, An approach to Cardiac Arrhythmia analysis Using Hidden Markov Models, IEEE Transactions on Biomedical Engineering. 1990, 37 (9):826-835.
U.S. Appl. No. 13/368,225.
U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
U.S. Appl. No. 61/480,532.
PCT/US2012/034330, International Preliminary Report on Patentability, Oct. 29, 2013.
PCT Application, PCT/US20013/020404, filed Jan. 4, 2013.
U.S. Appl. No. 14/261,651, filed Apr. 25, 2014.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/034333, International Preliminary Report on Patentability, Oct. 29, 2013.
PCT/US2012/034333, International Search Report, Aug. 29, 2013.
U.S. Appl. No. 13/424,429.
U.S. Appl. No. 13/424,479.
U.S. Appl. No. 13/424,525.
U.S. Appl. No. 61/480,528.
U.S. Appl. No. 61/480,530.
U.S. Appl. No. 61/480,535.
U.S. Appl. No. 61/480,539.
U.S. Appl. No. 61/480,541.
ISA Invitation to Pay Additional Fees, PCT/US2012/034323 mailed Aug. 2, 2012.
Roberts M, The regenerative dialysis (REDY) sorbent system, Nephrology, 1998, 275-278 : 4.

* cited by examiner

ION IMBALANCE DETECTOR

This application is a divisional application of U.S. patent application Ser. No. 11/349,540, filed Feb. 7, 2006, entitled "Ion Imbalance Detector," which has been granted as U.S. Pat. No. 8,903,492, the entire contents of which is incorporated herein by reference. Application Ser. No. 11/349,540 claims the benefit of now expired U.S. provisional application Ser. No. 60/650,497, filed Feb. 7, 2005, the entire content of which is incorporated herein by reference.

This application is related to now abandoned U.S. patent application Ser. No. 11/349,058, filed Feb. 7, 2006, entitled "Potassium Monitoring," the entire content of which is incorporated herein by reference.

TECHNICAL FIELD

The invention relates to systems and methods associated with monitoring physiological conditions, and in particular, to systems and methods associated with monitoring concentrations of ions in extracellular fluid.

BACKGROUND

The concentration of ions, such as potassium, sodium, chloride, and calcium, in the extracellular fluid (ECF) of a patient is of clinical significance. Abnormal ion concentration levels in the ECF can be a product of the pharmacological management of patients with heart failure. In general, the concentration of potassium and calcium ions in the intracellular fluid (ICF) of cardiac muscle or other tissue is high in comparison to potassium and calcium ions in the ECF. In contrast, the concentration of chloride and sodium ions is greater in the ICF than the ECF. As an example, elevated potassium ion concentration, denoted [$K^+$], in the ECF causes a reduced concentration gradient between ICF and ECF. A reduction of the resting membrane potential is associated with the reduction in the concentration gradient, often resulting in ectopic foci and arrhythmia.

A reduction in concentration gradient further affects the magnitude and duration of the action potential. The change in membrane potential caused by an action potential, which is about 120 mV in healthy cardiac muscle, can be reduced substantially. In addition, the duration of the action potential, which is about 250 milliseconds in healthy cardiac tissue, can be diminished.

The concentration of ions may have additional clinical significance as well, and for some patients the certain ion concentrations may be an important factor worth monitoring. For example, trauma patients, burn patients, diabetic patients with ketoacidosis, renal patients on dialysis, patients experiencing pulmonary edema, and cardiac arrest patients may have electrolyte fluctuations, particularly fluctuations of potassium ion concentrations. In addition, potassium ion retention accompanies the onset of some medical conditions, such as Addison's disease.

SUMMARY

In general, the invention is directed to methods and devices for determining a concentration of one or more ions in extracellular fluid of a patient. As examples, the ion may be any of potassium, sodium, chloride, or calcium. Further, as other examples, the ions may be drugs that result in ions in the blood or extracellular fluid, small molecules, or endogenously charged molecules. A system includes electrodes, and at least one of the electrodes is deployed in or near a tissue of the patient. The tissue may be a skeletal muscle, such as the pectoral muscle. A pulse generator supplies one or more stimulations to the tissue, and a sensor detects the response of the tissue to the stimulations. A processor determines a concentration of potassium ion as a function of the response.

As used herein, determining a concentration of ions in extracellular fluid of the patient includes, but is not limited to, determining an absolute concentration, such as measuring or estimating a molarity. Determining a concentration of ions can also includes determining a relative concentration, such as a concentration with respect to a baseline. Furthermore, determining a concentration of ions can include determining a change in concentration over time. In any case, the system may detect an ion imbalance in a patient.

The invention can be implemented as a stand-alone ion imbalance detection system. The invention can also be implemented in conjunction with an implantable medical device such as a cardiac pacemaker, cardioverter-defibrillator, patient monitor, drug pump or neurostimulator. The invention can be implemented as an external system or a system having external and implantable elements.

In one embodiment, the invention presents a system comprising a pulse generator configured to generate an electrical stimulation, an electrode configured to deliver the electrical stimulation to a tissue, such as a skeletal muscle, in a patient. The system further includes a sensor configured to detect at least one response of the tissue to the electrical stimulation, and a processor configured to determine a concentration of ions in extracellular fluid of the patient as a function of the response. The processor can be configured to determine a concentration of ions as a function of a sustained contraction of the tissue, for example, or a rippled contraction of the tissue, a rate of relaxation of the tissue, a pulse width of the response, the occurrence of summation in the response or the amplitude of the response. The system can be external, partially implantable or fully implantable.

In another embodiment, the invention is directed to a method that includes delivering an electrical stimulation to a tissue in a patient, detecting a response of the tissue to the electrical stimulation, and determining a concentration of ions in extracellular fluid of the patient as a function of the response. The method can further include delivering a therapy to the patient as a function of the response.

In a further embodiment, the invention is directed to a method comprising delivering an electrical stimulation to a tissue in a patient, detecting at least one response of the tissue to the electrical stimulations and storing a relationship between a concentration of ions in extracellular fluid of the patient and the response. The electrical stimulation can be delivered to the cardiac muscle, skeletal muscle, smooth muscle, nerve tissue, or skin of the patient. The stored response can be a sustained contraction of the tissue, for example, or a rippled contraction of the tissue, a rate of relaxation of the tissue, a pulse width of the response, the occurrence of summation in the response or the amplitude of the response. The absolute concentration of one or more ions can be determined and stored, and the relative concentrations of two or more ions can be determined and stored. This method is useful for calibrating an ion imbalance detection system according to the invention.

In a further embodiment, the invention is directed to a system comprising a control unit configured to control a pulse generator to deliver an electrical stimulation to a tissue in a patient and a processor configured to receive a signal indicative of a response of the tissue to the electrical stimulations and to store a relationship between the concentration of ions in extracellular fluid and the response in a non-transitory computer readable medium. The system can further receive data concerning a measured concentration of ions in the extracellular fluid and correlate the measured concentration with the response. The system can receive the signal by radio frequency or a wire transmitted signal. The processor can be configured to transmit the relationship between the concentration of ions and the response to an external computing device.

Additional embodiments of the invention include transitory or non-transitory computer-readable media comprising instructions that cause a programmable processor to carry out any of the methods of the invention.

The invention may result in one or more advantages. Compared to conventional techniques for detecting ion concentrations, the invention offers convenience and supports long-term implantation. Tests that rely upon laboratory analysis of blood samples require that blood be drawn from the patient, and may not be available outside a hospital setting. Electrochemistry-based ion sensors, such as sensors for potassium, are implantable. However, these ion sensors have not proven to be stable over long periods, and their performance degrades over time. Optical sensors for ion concentrations typically call for periodic replacement of components, such as a disposable strip used for making measurements. By contrast, the invention can be implanted, can conveniently monitor ion concentrations, and can remain reliable for extended periods of time.

In addition, the invention can be implemented within an IMD that delivers therapy, such as a pacemaker or drug pump, or supports other monitoring functions. Many patients experiencing heart failure, for example, can benefit from the implantation of an IMD that can monitor ion concentrations and apply one or more pacing therapies. The invention can offer the further advantage of implementation with one or more external elements, which can be deployed without surgery.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
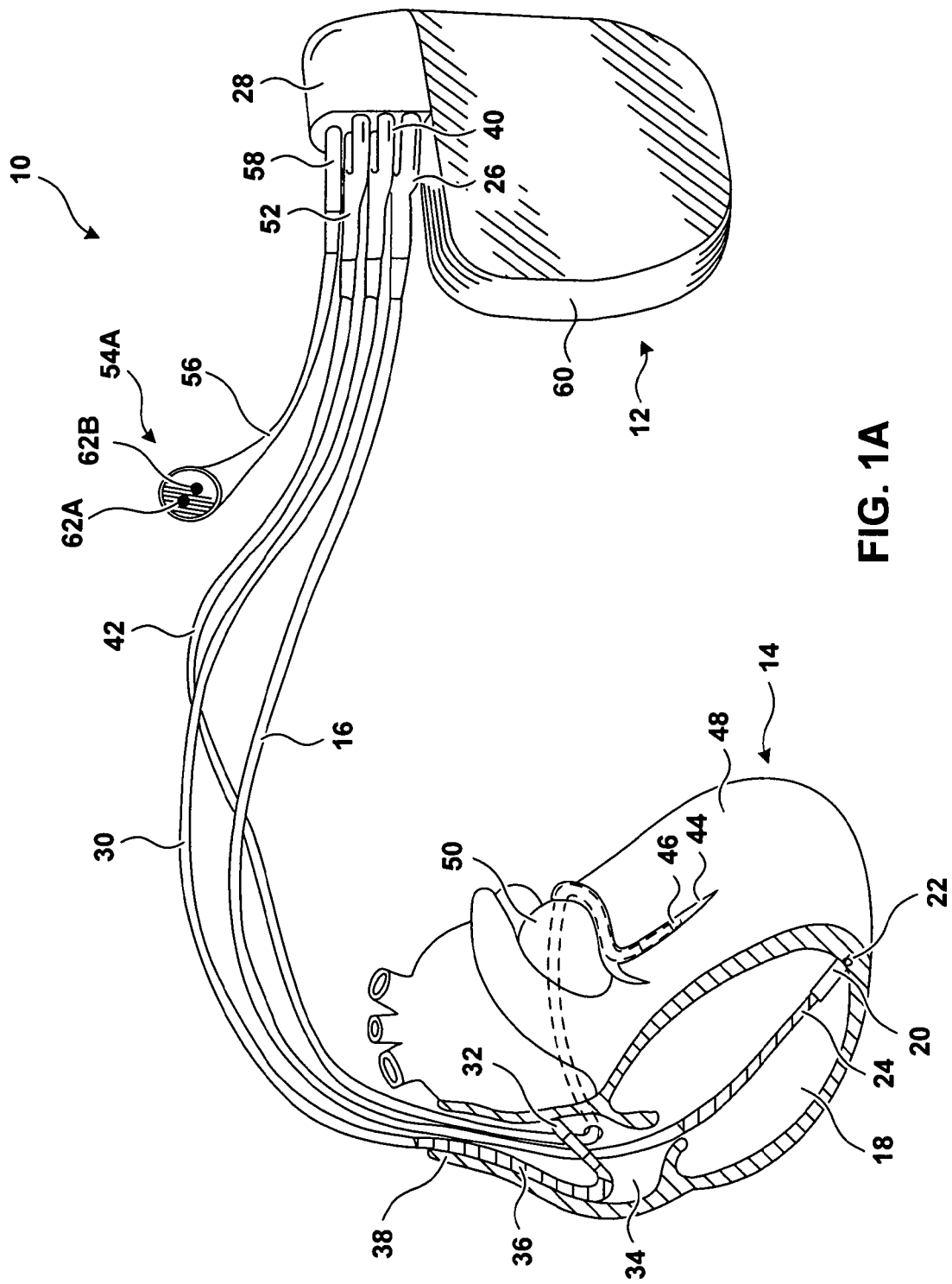
FIG. 1A is a schematic illustration of a human heart in conjunction with an exemplary implantable medical device and an exemplary electrode element according to an embodiment of the invention.

FIG. 1A is a schematic illustration of an exemplary embodiment of a system 10 that includes an implantable medical device (IMD) 12 in relationship to a heart 14 of a patient. IMD 12 is configured to be implanted in a human or animal body. As depicted in FIG. 1A, IMD 12 comprises a multi-chamber pacemaker having cardioversion and defibrillation capabilities. Although it can be advantageous to implement the invention with a multi-chamber pacemaker, the invention is not limited to the particular IMD shown. Furthermore, as discussed below, the invention need not be implemented as an implantable medical device. The invention can be implemented as a stand-alone ion monitor system, or in conjunction with a different type of implantable or external device such as a patient monitor, drug pump, muscle stimulator or neurostimulator. The ion whose concentration is monitored may be any one of potassium ($K^+$), sodium ($Na^+$), chloride ($Cl^-$), or calcium ($Ca^{2+}$). Other ions may include magnesium ($Mg^{2+}$), bicarbonate ($HCO_3^-$), or any other ions found in intracellular fluid (ICF) or extracellular fluid (ECF). Further, other ions may include drugs that result in ions in the blood or extracellular fluid, small molecules, or endogenously charged molecules.

A right ventricular lead 16 includes an elongated insulative lead body carrying one or more concentric coiled conductors separated from one another by tubular insulative sheaths. The distal end of right ventricular lead 16 is deployed in the right ventricle 18 of heart 14. Located adjacent the distal end of the lead body are one or more pace/sense electrodes 20, which are configured to deliver cardiac pacing and are further configured to sense depolarizations of right ventricle 18. A fixation mechanism 22 such as tines or a screw-in element, anchors the distal end in right ventricle 18. The distal end also includes an elongated coil electrode 24 configured to apply cardioversion or defibrillation therapy. Each of the electrodes is coupled to one of the coiled conductors within the lead body. At the proximal end of right ventricular lead 16 is a connector 26, which couples the coiled conductors in the lead body to IMD 12 via a connector module 28.

A right atrial lead 30 includes an elongated insulative lead body carrying one or more concentric coiled conductors separated from one another by tubular insulative sheaths corresponding to the structure of right ventricular lead 16. Located adjacent the J-shaped distal end of right atrial lead 30 are one or more pace/sense electrodes 32, which are configured to sense depolarizations of and deliver pacing stimulations to right atrium 34. As shown in FIG. 1A, an elongated coil electrode 36 is provided proximate to the distal end of right atrial lead 30, and is located in right atrium 34 and the superior vena cava 38. At the proximal end of the lead is a connector 40, which couples the coiled conductors in right atrial lead 30 to IMD 12 via connector module 28.

A coronary sinus lead 42 includes an elongated insulative lead body deployed in the great cardiac vein 44. The lead body carries one or more coiled conductors coupled to one or more pace/sense electrodes 46. Electrodes 46 are configured to deliver ventricular pacing to left ventricle 48 and are further configured to sense depolarizations of left ventricle 48. Additional pace/sense electrodes (not shown) may be deployed on coronary sinus lead 42 that are configured to pace and sense depolarizations of the left atrium 50. At the proximal end of coronary sinus lead 42 is connector 52, which couples the coiled conductors in coronary sinus lead 42 to connector module 28.

An exemplary electrode element 54A is coupled to the distal end of a lead 56. Lead 56 carries one or more conductors separated from one another by insulative sheaths. A connector 58 at the proximal end of the lead couples the conductors in lead 56 to IMD 12 via connector module 28.

In addition to connector module 28, IMD 12 comprises a housing 60 formed from one or more materials, including conductive materials such as stainless steel or titanium. Housing 60 may include insulation, such as a coating of parylene or silicone rubber, and in some variations, all or a portion of housing 60 may be left uninsulated. The uninsulated portion of housing 60 can serve as a subcutaneous electrode and a return current path for electrical stimulations applied via other electrodes.

In the embodiment shown in FIG. 1A, electrode element 54A includes two electrodes 62A and 62B. At least one of electrodes 62A and 62B is deployed in or near test tissue and delivers stimulation to the tissue, while the other provides a return current path. In the embodiment shown in FIG. 1A, electrodes 62A and 62B are button electrodes, but the invention encompasses other electrode types as well. The invention will be described in terms of stimulation of muscle cells, but the invention can encompass other test tissues as well. The test tissue can comprise a collection of autologous or non-autologous cells that are sensitive to the concentration of the selected ion. For example, the test tissue may be one of cardiac muscle, skeletal muscle, smooth muscle, nerve tissue, skin, or the like. The ions may be one of $K^+$, $Na^+$, $Cl^-$, $Ca^{2+}$, $Mg^{2+}$, or $HCO_3^-$. Additionally, possible ions may include drugs (such as Digitalis) that become ions in the blood or ECF, small molecules, endogenously charged molecules, or other molecules in their ionic forms. Concentrations of ions will be depicted with brackets such as $[K^+]$, as in the example of the concentration of potassium ions. While $[K^+]$ is discussed in detail as an exemplary ion concentration herein, any other ion concentrations may be additionally or alternatively detected according to the invention.

As described below, IMD 12 includes one or more implantable pulse generators (IPGs) (not shown in FIG. 1A) configured to generate stimuli to be delivered to one or more muscles of the patient via electrode element 54A. As described below, skeletal muscle is generally the most desirable tissue, because it is usually readily accessible and response of skeletal muscle can be readily related to ion concentration. Furthermore, it may be desirable to stimulate skeletal muscles that do not get much use and are less prone to fatigue. The invention encompasses embodiments in which stimulation and response of other kinds of tissue can be related to ion concentration, but muscle tissue, such as skeletal muscle tissue is the exemplary tissue described herein.

Further, as discussed above, the invention encompasses monitoring other ion concentrations instead of or in addition to $[K^+]$. For example, $[Na^+]$ or $[Cl^-]$ may be detected when monitoring skeletal muscle due to the large concentration gradient between the ICF and ECF. The invention encompasses monitoring the concentration of any ion in the ECF or ICF based on the electrical and/or mechanical response of any tissue to a stimulus.

Housing 60 may include one or more sensors (not shown in FIG. 1A) configured to detect at least one response of the stimulated muscle to the electrical stimulation or stimulations. In some embodiments, the sensor may be deployed elsewhere, such as on the distal end of lead 56. In general, the sensor detects the electromechanical response of the stimulated muscle. Examples of sensors will be described below.

In general, the distance between electrodes 62A and 62B can be a function of the pulse magnitude generated by an IPG, a target stimulation magnitude, and the kind of electrodes employed. For example, to deliver a stimulus with a field strength of 10 volts per centimeter (V/cm) using IMD 12 which is capable of producing 2 V pulses, electrodes 62A and 62B can be separated by two millimeters. The invention is not limited to any particular physical dimensions or stimulation magnitudes, however.

IMD 12 also includes one or more IPGs configured to generate pacing stimuli to be delivered to one or more chambers of heart 14. The IPGs that stimulate heart 14 may be, but need not be, the same IPG that generates muscle stimulations. IMD 12 further includes one or more processors (not shown in FIG. 1A) that regulate the delivery of pacing pulses. The processor in IMD 12 is configured to apply a variety of pacing modes, including therapies that may be beneficial for patients suffering from heart failure, such as cardiac potentiation therapy (CPT) or cardiac resynchronization therapy (CRT). CPT generally involves electrically stimulating one or more heart chambers to induce post-extrasystolic potentiation, and CRT involves delivering pacing pulses to one or both ventricles to synchronize ventricular contractions.

Figure 1B:
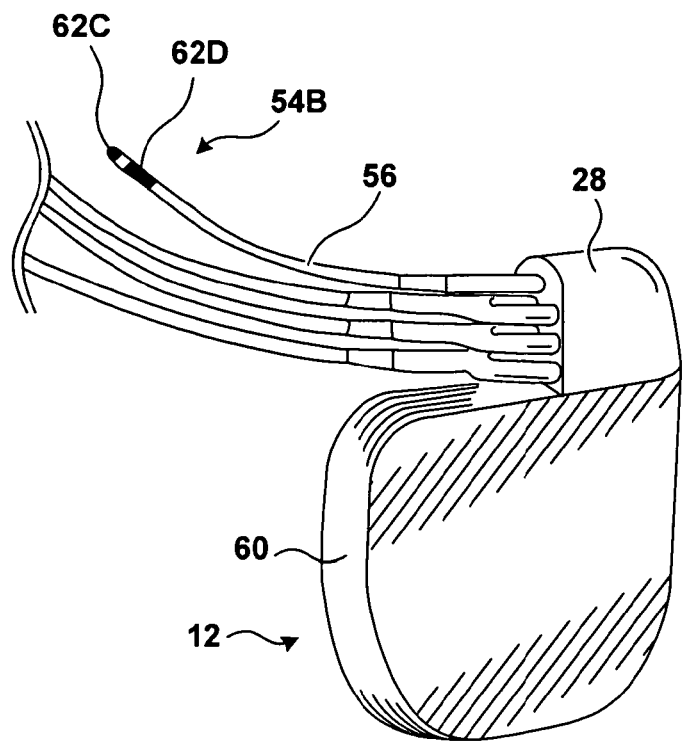
FIGS. 1B through 1E are schematic illustrations of an implantable medical device with alternate embodiments of electrode elements.

FIG. 1B is a schematic illustration of IMD 12, with an alternate embodiment of an electrode element 54B. In the embodiment depicted in FIG. 1B, electrode element 54B, like electrode element 54A, is coupled to the distal end of lead 56, which carries one or more conductors separated from one another by insulative sheaths and is coupled to connector module 28 via connector 58. Electrode element 54B includes two electrodes 62C and 62D, which deliver electrical stimulation to muscle, or other tissue sensitive to $[K^+]$, and provide a return current path. In other embodiments, electrodes 62C and 62D may deliver electrical stimulation to the same tissue or another tissue sensitive to a different ion concentration, such as $[Na^+]$ or $[Cl^-]$.

Electrode element 54B resembles a pace/sense electrode, such as pace/sense electrode 32 in FIG. 1A, in that electrode element 54B includes a tip electrode 62C and a ring electrode 62D. Dimensions of electrode element 54B may be comparable to those of conventional pace/sense electrodes. Although not shown in FIG. 1B, the distal end of lead 56 may include one or more fixation mechanisms configured to prevent or reduce lead migration.

Figure 1C:
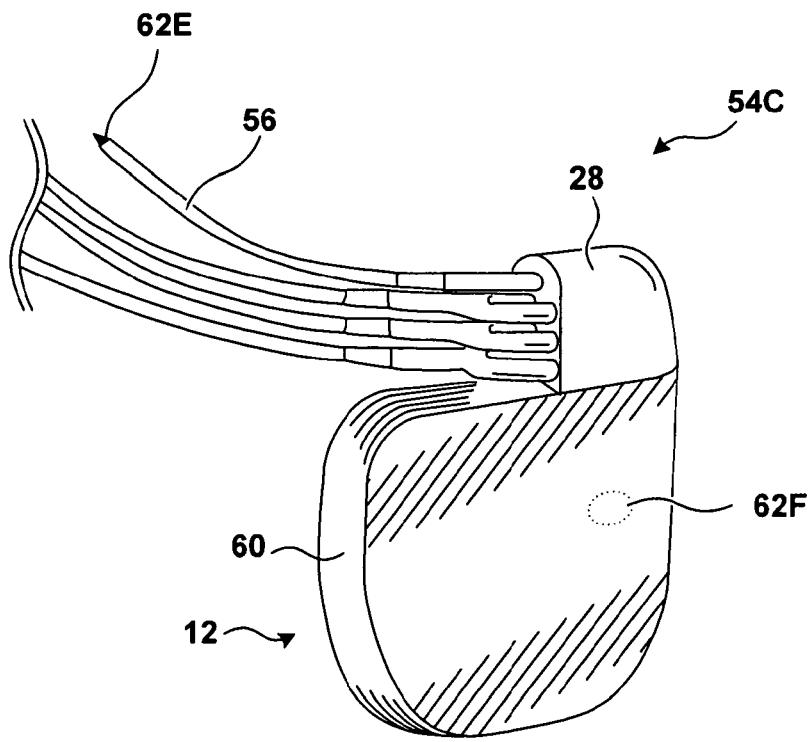

FIG. 1C is a schematic illustration of IMD 12, with another alternate embodiment of an electrode element 54C. In the embodiment depicted in FIG. 1C, electrode element 54C includes an electrode 62E deployed at the distal end of lead 56, and another electrode 62F in the body of housing 60. Housing electrode 62F can be deployed at any site in housing 60. Lead electrode 62E is configured to generate an intense electrical field at the site of stimulation. A point at the distal end of lead electrode 62E causes the electric field to be more intense at the point, which can improve the likelihood of stimulation of muscle tissue or other tissue sensitive to the concentration of an ion of interest, such as $[K^+]$. The distal end of lead 56 may include one or more fixation mechanisms configured to prevent or reduce lead migration.

Figure 1D:
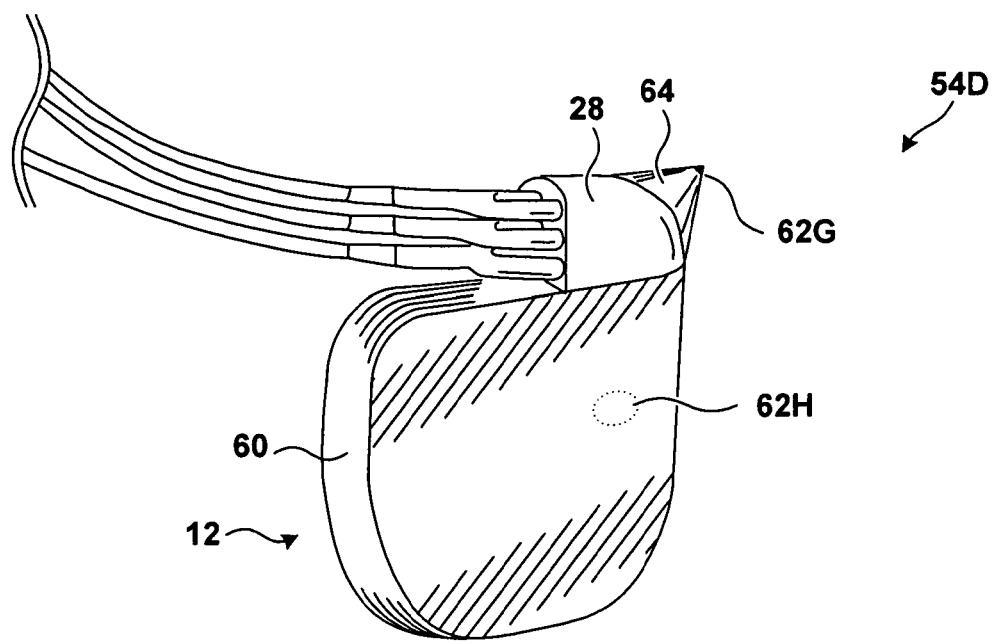

FIG. 1D is a schematic illustration of IMD 12, with an additional alternate embodiment of an electrode element 54D. Electrode element 54D includes an electrode 62G deployed on a fixed mount 64. In the embodiment depicted in FIG. 1D, fixed mount 64 is coupled to connector module 28, but fixed mount 64 may also be deployed elsewhere on IMD 12. Exemplary electrode 62G, like electrode 62E in FIG. 1C, is configured to generate an intense electrical field at the site of stimulation. Another electrode 62H is deployed in the body of housing 60.

As discussed below, some implantations if IMD 12 may place IMD 12 in direct contact with muscle such as skeletal muscle. The embodiment depicted in FIG. 1D may be desirable in such implantations, as electrodes 62G and 62H can be deployed without leads.

Figure 1E:
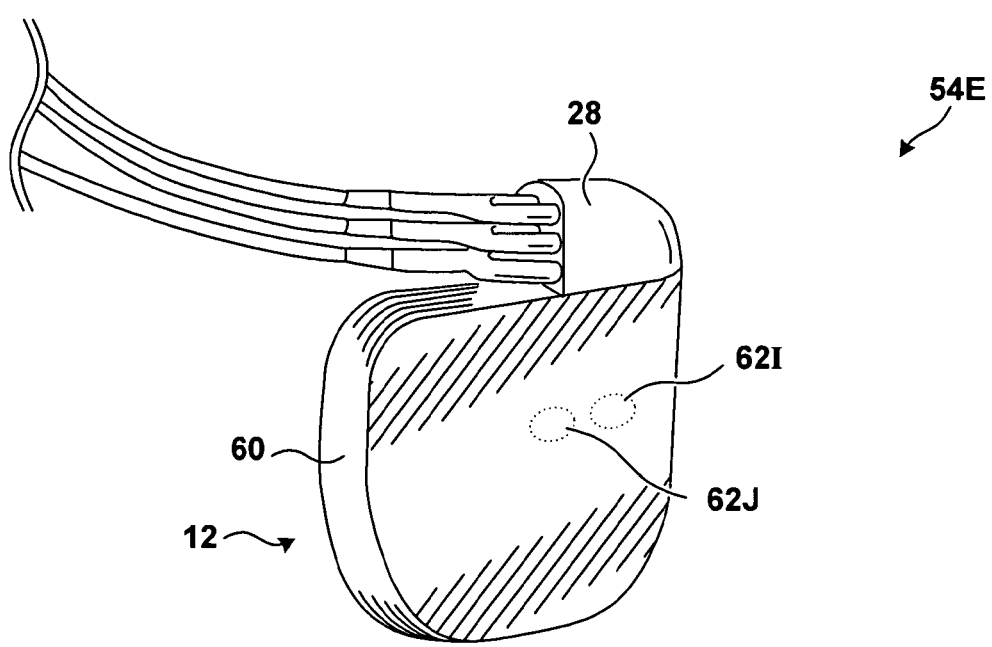

FIG. 1E is a schematic illustration of IMD 12, with a further alternate embodiment of an electrode element 54E. Electrode element 54E includes two electrodes 62I and 62J deployed in housing 60. In a variation of this embodiment, housing 60 may include an array of three or more electrodes. As with the embodiment shown in FIG. 1D, the embodiment shown in FIG. 1E may be desirable in implantations in which IMD 12 is implanted in direct contact with muscle or other ion concentration sensitive tissue.

Figure 1F:
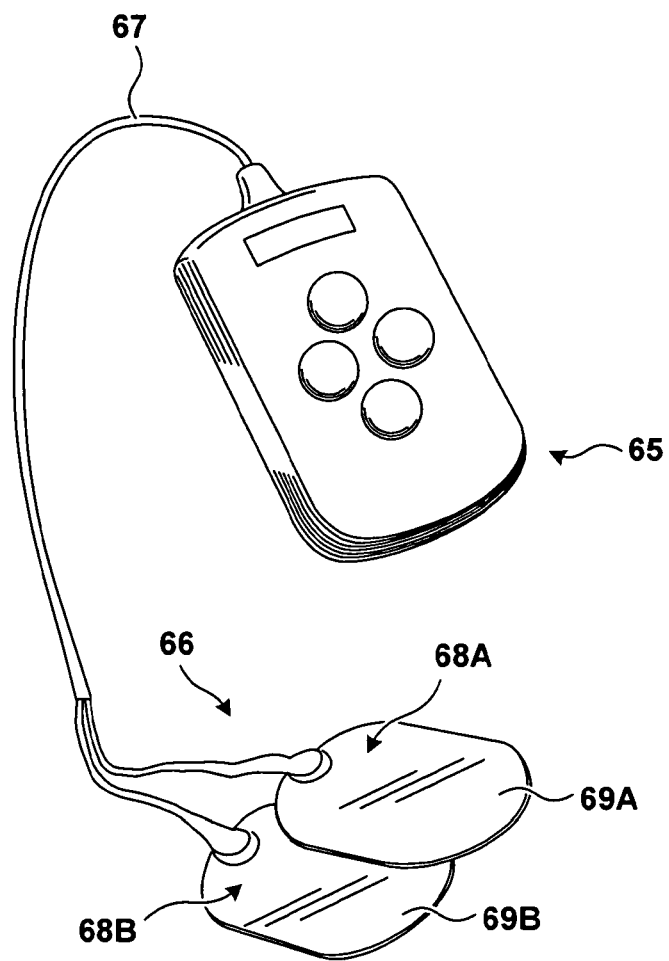
FIG. 1F is a schematic illustration of an exemplary external medical device and an exemplary electrode element according to an embodiment of the invention.

FIG. 1F is a schematic illustration of a further embodiment of the invention, in which one or more elements are external and are not configured to be implantable in a human or animal body. In the embodiment depicted in FIG. 1F, external medical device 65 includes one or more IPGs (not shown in FIG. 1F) configured to generate stimuli to be delivered to one or more muscles of the patient via electrode element 66. Examples of medical devices that can be configured to generate stimuli to be delivered to muscles via an electrode element are a Transcutaneous Electrical Nerve Stimulation (TENS) unit, an Electronic Muscle Stimulation (EMS) unit and an electro-acupuncture unit. The invention is not limited to such medical devices, however. Medical device 65 or electrode element 66 may also include one or more sensors (not shown in FIG. 1F) configured to detect an electromechanical response of the stimulated muscle to the electrical stimulation or stimulations. In a variation, a sensor module distinct from device 65 or electrode element 66 may be deployed on the patient's skin to detect the electromechanical response.

Electrode element 66 is coupled to medical device 65 via lead 67. Electrode element 66 includes two electrodes 68A and 68B, which deliver electrical stimulation to muscle, or other tissue sensitive to [K$^+$] or another ion concentration, and provide a return current path. In the example of FIG. 1F, electrodes 68A and 68B are deployed externally with adhesive pads 69A and 69B, which adhere to the skin. Electrodes 68A and 68B may deliver an electrical stimulation to any of several tissues, especially skeletal muscles located beneath the skin. Although the embodiment shown in FIG. 1F is completely external with no implantable elements, the invention encompasses embodiments that have external and implantable elements.

The invention is not limited to the particular embodiments depicted in FIGS. 1A through 1F. For purposes of discussing the invention and its operation, the description below will focus principally upon implantable embodiments, and in particular, the embodiment depicted in FIG. 1A. Further, as discussed above, the invention is not limited to stimulation of skeletal muscle tissue, or stimulation via leads or electrodes that are separate from the leads or electrodes used to deliver therapeutic stimulation. In other words, ion imbalance may be determined directly in the organ of interest without the use of an additional stimulation pulse or stimulation lead. For example, in some embodiments, ion imbalance may be monitored by detecting the response of cardiac muscle to the therapeutic pacing stimuli delivered to heart 14. Further, CPT may be used to determine an ion concentration. CPT therapy provides an additional stimulus near the time of the T wave of the cardiac electrical signal to create a stronger ventricular contraction of heart 14. The response to the stimulus may be sensitive to [Ca$^{2+}$], but other ion concentrations may be determined as well.

Figure 2:
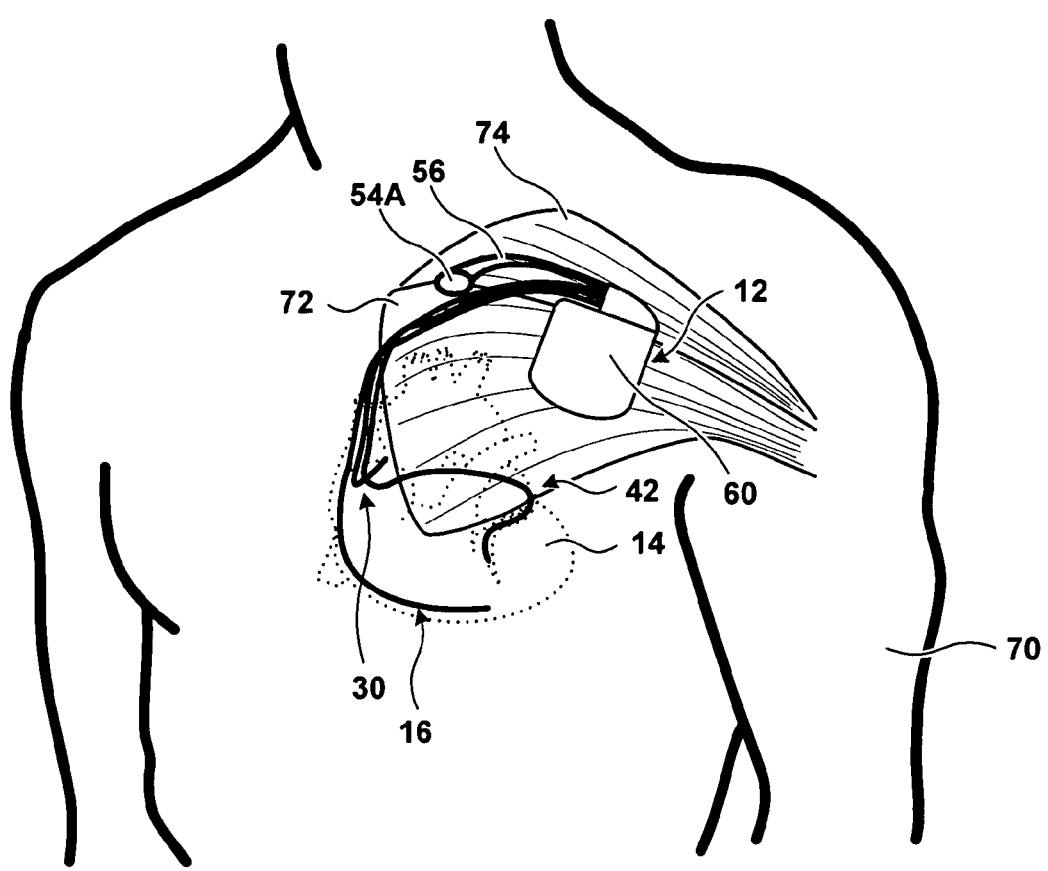
FIG. 2 is a schematic illustration of an implantation of an exemplary implantable medical device and an exemplary electrode element proximate to skeletal muscle.

FIG. 2 is a schematic illustration of an exemplary implantation in a patient 70 of the apparatus depicted in FIG. 1A. Right ventricular lead 16, right atrial lead 30 and coronary sinus lead 42 are deployed in heart 14 via access through a vein such as the subclavian vein (not shown). Electrode element 54A and lead 56, by contrast, do not enter the cardiovascular system.

Rather, electrode element 54A is deployed proximate to skeletal muscle. In the exemplary implantation depicted in FIG. 2, electrode element 54A is deployed proximate to the sternal portion 72 and clavicular portion 74 of the Pectoralis major. The invention also supports implantations in which electrode element 54A is deployed proximate to other skeletal muscles, other muscles, or other tissues sensitive to [K$^+$], [Na$^+$], [Cl$^-$], [Ca$^{2+}$], [Mg$^{2+}$], [HCO$_3^-$], or other ions in the ECF. When a surgeon implants IMD 12 in a pocket, such as a pocket proximate to the Pectoralis major according to a conventional implantation procedure, the surgeon can deploy electrode element 54A proximate to a desired skeletal muscle. Electrode element 54A may include a fixation mechanism such as a loop or Dacron mesh that allows the surgeon to anchor electrode element 54A in place with suture.

As shown in FIG. 2, housing 60 of IMD 12 is deployed in contact with pectoral muscles 72 and 74. A conventional implantation technique for some implantable devices, such as a pacemaker, provides for deploying IMD 12 in direct contact with pectoral muscle. In such implantations, embodiments such as those depicted in FIGS. 1D and 1E may be feasible.

Figure 3:
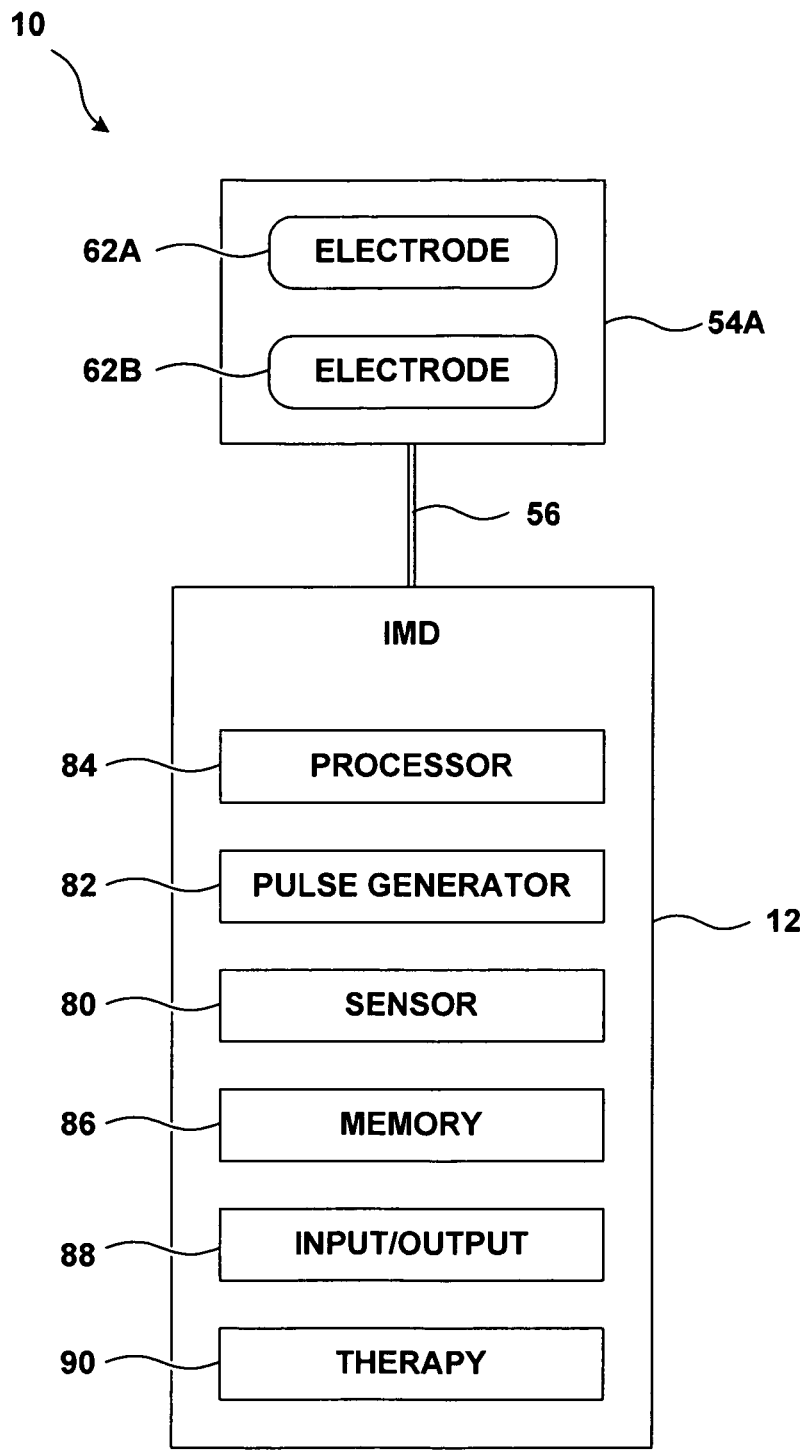
FIG. 3 is a block diagram showing a system that can deliver one or more electrical stimuli to a tissue and determine a concentration of ions in extracellular fluid as a function of the response to the stimuli.

FIG. 3 is a block diagram illustrating components of an exemplary system 10 such as the system depicted in FIG. 1A. Electrode element 54A includes electrodes 62A and 62B, which are configured to deliver one or more electrical stimulations to a muscle or other tissue sensitive to [K$^+$] or another ion concentration. In a typical embodiment, one of electrodes 62A and 62B introduces a stimulation from IMD 12 to a skeletal muscle, and the other of electrodes 62A and 62B provides the return current path.

In the embodiment shown in FIG. 3, IMD 12 includes a sensor 80 that detects the electromechanical response of the muscle to the stimulations delivered by electrodes 62A and 62B. Sensor 80 can detect the mechanical response, the electrical response, or both. Examples of mechanical responses are muscle tension, muscle strength, muscle density, muscle length and pressure generated by the muscle. Sensor 80 can be deployed inside housing 60 of IMD 12 or outside housing 60. Sensors such as an optical sensor could be configured to respond to one or more of these mechanical responses. An accelerometer, which responds to muscle movement, is another example of a sensor that can detect a mechanical response. In some embodiments of IMD 12, an accelerometer may be provided inside housing 60 to detect patient activity or posture. Such an accelerometer could also detect a mechanical response of stimulated muscle. In an external implementation such as that depicted in FIG. 1F, an accelerometer may be disposed in device 65, in electrode element 66, or as a separate module deployed on the patient's skin. Further examples of sensors that can detect a mechanical response are a pressure sensor and a piezoelectric sensor.

Sensor 80 can also be configured to detect an electrical response. In some embodiments of the invention, electrodes 62A and 62B not only deliver electrical stimulations to the muscle, but also convey the electrical response to sensor 80. An example of a sensor that detects an electrical response is an impedance sensor.

A pulse generator 82 in IMD 12 generates the stimulations that are delivered to the skeletal muscle via electrodes 62A and 62B. Pulse generator 82 may be, but need not be, the same component that generates pacing stimulations that are delivered to heart 14. Pulse generator 82 operates under the control of processor 84. Processor 84 can be embodied in one or more forms, such as a microprocessor, digital signal processor, application specific integrated circuit or full custom integrated circuit. In addition to controlling pulse generator 82, processor 84 receives and analyzes signals detected via sensor 80 that are indicative of the response of the muscle to the stimulations, and determines a concentration of potassium or other ions in extracellular fluid (ECF) of the patient as a function of the signals. Therefore, processor 84 can detect an ion imbalance in the patient. As discussed in more detail below, [$K^+$] in the ECF affects the response of the muscle or tissue being monitored. In other embodiments, processor 84 may determine a concentration of another ion, such as [$Na^+$], [$Cl^-$], [$Ca^{2+}$], [$Mg^{2+}$], [$HCO_3^-$], a drug, small molecule, or endogenously charged molecule. In the case of an ion other than potassium, sensor 80 may be calibrated differently to account for the detection of the selected ion concentration.

As used herein, determining a concentration of one or more ions in ECF of the patient can include determining an absolute concentration, such as measuring or estimating the molarity of ions. Determining a concentration of potassium ions can also include determining a relative concentration, such as a concentration with respect to a baseline. Furthermore, determining a concentration of potassium ions can include determining a change in concentration over time. In practice, monitoring a change in concentration over time has clear clinical advantages.

Processor 84 controls the scheduling of stimulations. Processor 84 may be configured to deliver the stimulations and monitor one or more ion concentrations when the patient is in bed, for example. Processor 84 may also be configured to deliver the stimulations and monitor the ion concentration a predetermined number of times each day.

Processor 84 may further be configured to determine whether conditions are suitable for delivering stimulations and monitoring the ion concentration. For example, it may be desirable to monitor [$K^+$] or other ion concentrations once a day when the patient is inactive, particularly when the patient's muscles or other tissues are relaxed and when there is less likelihood of extraneous motion that could affect sensor 80. When the patient is physically active, the physical activity can interfere with the monitoring of ion concentrations, such as [$K^+$]. Processor 84 may receive a signal from sensor 80 or from another sensor that generates a signal as a function of patient activity, such as an accelerometer. On the basis of the signal, processor 84 may determine whether the patient is too active or whether conditions are otherwise unsuitable for monitoring. When processor 84 determines that conditions are unsuitable, processor 84 may defer delivering stimulations and may reschedule the stimulations for a later time.

In addition, processor 84 may be programmed to deliver the stimulations and monitor ion concentration in response to an event. An exemplary event that could trigger delivery of stimulations and monitoring of an ion concentration, such as [$K^+$], is an arrhythmia. When IMD 12 is a pacemaker or other device configured to treat arrhythmia, IMD 12 may apply therapy to treat the arrhythmia, then deliver the stimulations and monitor [$K^+$], to determine whether potassium ion concentration might be contributing to the arrhythmia. Processor 84 can further be configured to control delivery of pacing therapy to heart 14. Another exemplary triggering event is the detection of a low level of physical activity indicative of the onset of rest or sleep.

Alternatively, processor 84 may be programmed to deliver the stimulations and monitor one or more ion concentrations, such as [$K^+$], to predict an arrhythmia based upon an ion imbalance. In this manner, as an example, IMD 12 may detect poor regulation of [$K^+$] and allow a physician to modify patient medication or suggest alternative diets. Exemplary medications may include anti-arrhythmic drugs, potassium channel inhibitors, or diets that include potassium sources such as bananas. In some embodiments, IMD 12 may notify the patient of an ion imbalance with an audible sound or stimulation so that the patient may take precautions before the arrhythmia.

In the embodiment depicted in FIG. 3, IMD 12 includes a memory element 86 configured to store information about ion concentrations. Memory element 86 can store information such as the time when electrical stimulations were administered, the frequency of the stimulations, the muscle's response to the stimulations, and the determined ion concentration. Memory element 86 can also store a history of such monitoring, and can store information concerning the change in ion concentration over time.

In other embodiments, IMD 12 may detect more than one ion concentration at one time in the form of individual concentrations or concentration ratios. This multiple ion imbalance detection may be performed with multiple sensors 80 or derived from the tissue response. In any case, memory element 86 may store instructions for processor 84 to perform the multiple ion imbalance detection and store any data generated by the detection.

Further, memory element 86 may store instructions that cause a programmable processor, such as processor 84, to carry out techniques for monitoring potassium ion concentration. Memory element 86 may include but is not limited to read-only memory, random access memory, Flash memory, EPROM and a magnetic or optical storage medium, or any combination thereof.

When processor 84 determines that an ion concentration or ion imbalance is such that physiological functioning may be adversely effected, or is otherwise a cause for concern, processor 84 may take action. As an example, if the processor determines that [$K^+$] in ECF is elevated to the point that heart function may be adversely affected, or when processor 84 determines that [$K^+$] in ECF is rising to a point of concern, the processor may take action. Processor 84 may, for example, send a notification via an input/output element 88. Input/output element 88 comprises one or more elements that relay the message to the patient, the patient's physician, or any other person or monitoring device. Input/output element 88 can include, for example, a radio frequency (RF) transmitter, an inductive coil transmitter or an audible alarm. For example, input/output element 88 may issue a warning to patient 12 if the determination of an ion concentration is above or below a predetermined threshold.

Additionally, whether or not a determination that patient function may be adversely affected has been made, input/output element 88 may transmit data stored by memory element 86, i.e. ion concentration information or system 10 status data, to another computing device such as a notebook computer, hand held computer, physician programmer, personal computer, or network server. The data may be transmitted for analysis and/or storage. In the case of a network server, the data may be further forwarded to a hospital, clinic, manufacturer of IMD 12, or another location where the data may be analyzed or stored.

When processor 84 determines that ion concentration or imbalance in ECF is of concern, processor 84 can also control the delivery of therapy via a therapy element 90. Therapy element 90 can include, for example, an implantable drug delivery device that delivers a drug to the patient. The drug may be a diuretic, for example. As the patient's body loses water due to increased urinary output, the patient's arterial blood pressure declines, reducing the workload of heart 14. In addition, increased urinary output enhances elimination of $K^+$ and other ions. Therapy element 90 can work in concert with input/output element 88. For example, therapy element 90 can administer a drug while input/output element 88 can notify the patient that the patient should take an action, such as contacting his physician or controlling the potassium in his diet.

Therapy element 90 can also encompass elements that pace heart 14 via leads 16, 30 and 42, or any combination thereof, as depicted in FIGS. 1A and 2. In general, however, pacing therapies would probably not be applied to address or control $[K^+]$ or other ion concentrations. Although pacing therapies such as cardiac resynchronization and bi-ventricular pacing may be of benefit to patients having heart failure, such pacing therapies would not ordinarily be administered in response to elevated $[K^+]$. Some pacing therapies can cause $[K^+]$ to become even more elevated. Accordingly, although it is unlikely that processor 84 would apply pacing therapies to address elevated $[K^+]$, processor 84 may monitor $[K^+]$ to determine whether such pacing therapies ought to be employed or discontinued. In other words, processor 84 may monitor $[K^+]$ or other ion concentrations to determine whether pacing therapies are likely to be safe and effective.

Figure 4A:
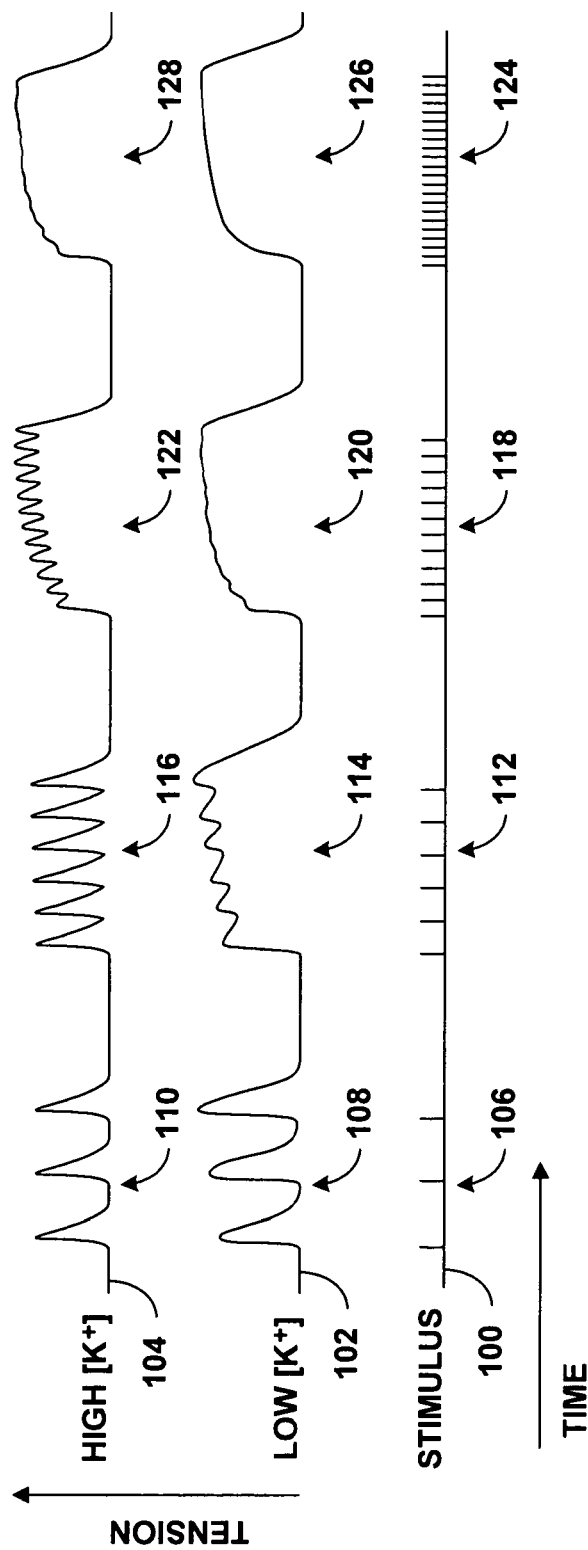
FIGS. 4A and 4B are timing diagrams illustrating stimuli and the responses of skeletal muscle thereto, according to various embodiments of the invention.
Figure 4B:
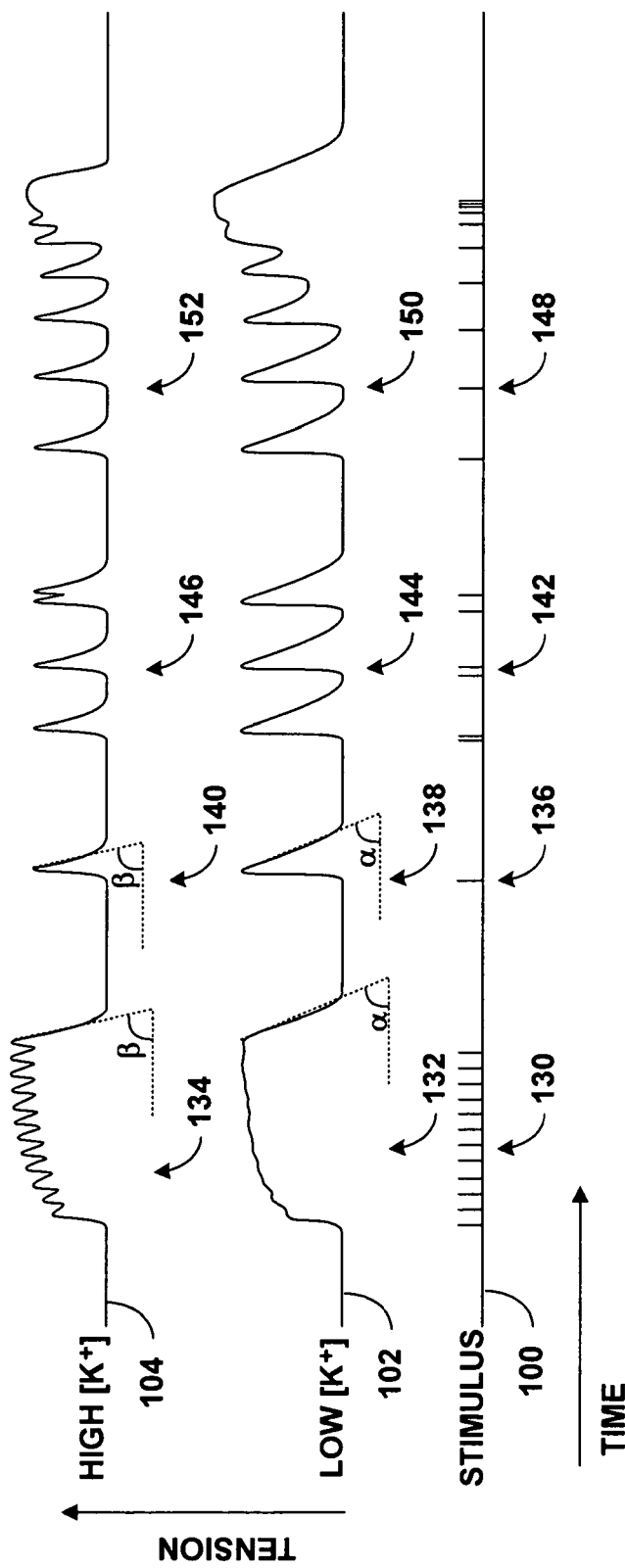

FIGS. 4A and 4B are timing diagrams that illustrates exemplary techniques by which processor 84 can determine a concentration of potassium ion, as an example ion, in ECF as a function of the response of skeletal muscle, as an example tissue, to stimulations from an electrode element such as electrode elements 54A-E. Each stimulus may have an amplitude of about two to twenty volts, for example, and a pulse width of about 0.1 to 1.0 milliseconds. Stimulus line 100 shows the timing of stimuli generated by pulse generator 82 delivered to the skeletal muscle via electrodes such as electrodes 62A-62J. Response line 104 depicts a response of skeletal muscle to the stimulations in an environment where $[K^+]$ is low relative to concentrations in ICF. In other words, response line 104 depicts a response of skeletal muscle in a "normal" patient. By contrast, response line 104 depicts a response of skeletal muscle in a patient having elevated $[K^+]$. A patient having elevated $[K^+]$ is not normal and is at risk of heart failure.

For purpose of illustration, the response is depicted as muscle tension. Other responses, such as muscle motion or muscle length, may also be evaluated, although the response waveforms may look different from those in FIGS. 4A and 4B. In addition, the response waveforms may look different from those in FIGS. 4A and 4B depending upon the muscle or other tissue being stimulated. For example, in embodiments that monitor the response of nervous tissue to the stimulation as a means for monitoring ion concentration, the response waveform may include one or more action potentials Stimuli can be delivered in a range of frequencies, such as from about 10 Hz to about 150 Hz. A first set of stimuli 106 at a low frequency produces similar but distinct responses in normal $[K^+]$ and elevated $[K^+]$ environments. Contractions 108 in a normal muscle and contractions 110 in a muscle in an environment of elevated $[K^+]$ are indicated by muscle tension as a function of time. In comparison to one another, contractions 108 in a normal muscle have a longer duration and may also exhibit some summation. In the example of FIG. 4A, contractions 108 also exhibit a greater amplitude. In contrast, contractions 110 in an elevated $[K^+]$ environment are of a smaller amplitude, a shorter duration and exhibit little or no summation.

A second set of stimuli 112 at a higher frequency produces distinct responses in normal $[K^+]$ and elevated $[K^+]$ environments as well. Contractions 114 in a normal muscle exhibit marked summation. The muscle approaches tetanus, but, as depicted in FIG. 4, the frequency of stimulation is too low to produce a sustained tetanic response. Instead, muscle contractions 114 exhibit "ripples" or wavering, rather than the sustained contraction of tetanus. In contrast with contractions 114, contractions 116 in an elevated $[K^+]$ exhibit little or no summation.

A third set of stimuli 118 at an even higher frequency produces contractions 120 in a normal muscle that show a tetanic response. In particular, muscle tension rises steadily to a maximum and levels off. Contractions 122 in an elevated $[K^+]$ environment, by contrast, exhibit summation, but the rise in tension is rippled and tension is not sustained. In other words, stimuli 118 produce a sustained response 120 in a normal $[K^+]$ environment, but produce a rippled response 122 in an elevated $[K^+]$ environment.

The frequency of third set of stimuli 118 can be used to distinguish a normal $[K^+]$ environment from an elevated $[K^+]$ environment. The distinction can be achieved in a number of ways. For example, an analog or digital highpass filter may be employed to detect whether a ripple is present. Fourier or wavelet analysis may be used to detect the presence of high frequency components. Template matching or other morphological analysis may be performed. Other forms of analog or digital signal analysis may be used to detect the presence of a rippled response.

A fourth set of stimuli 124 at an even higher frequency produces contractions 126 in a normal muscle and contractions 128 in an elevated $[K^+]$ environment that are similar, in that both exhibit a tetanic response. Consequently, stimuli at this frequency would be less desirable for distinguishing a normal $[K^+]$ environment from an elevated $[K^+]$ environment.

FIG. 4B shows additional distinction techniques. A set of stimuli 130 evokes responses 132, 134 similar to responses 120, 122 in FIG. 4A. In FIG. 4B, the quantity of interest is the decline of the response following cessation of stimulation, which indicates how fast the stimulated muscle relaxes. In FIG. 4B, the decline is indicated by angles $\alpha$ and $\beta$ of lines tangent to the responses. In general, the response returns to resting more quickly in an elevated $[K^+]$ environment and more slowly in a normal $[K^+]$ environment, so angle $\beta$ is generally larger and indicative of a greater slope than angle cc. Another measurement of the decline of the response is the fall time, i.e., the time for the response to decrease from one value to another. Fall time can be determined by measuring the time it takes for the response to fall from its peak value to half its peak value, for example, or the time it takes for the response to fall from ninety percent of its peak value to ten percent of its peak value. The signal decays more quickly in elevated $[K^+]$ environment and more slowly in a normal $[K^+]$ environment, so the fall time in the elevated $[K^+]$ environment is smaller than the fall time in a normal $[K^+]$ environment. Processor 84 may detect the rate of muscle relaxation with any analog or digital technique, such as taking a difference at discrete points, measuring the time between high and low values, or differentiating the response waveform.

It may be possible to observe the decline with a single stimulus. Stimulus 136 evokes responses 138, 140. In addition to monitoring fall time or slope as described above, processor 84 may detect the pulse width or action potential duration of the response. Because the response returns to resting more quickly in an elevated [$K^+$] environment than in a normal [$K^+$] environment, the pulse width of the in an elevated [$K^+$] environment is narrower than in a normal [$K^+$] environment. The narrower pulse width is associated with the shorter refractory period in an elevated [$K^+$] environment. Narrower pulse width in an elevated [$K^+$] environment has been demonstrated with both cardiac muscle and skeletal muscle.

A set of stimuli 142 illustrates another distinction technique. This process includes delivering pairs of stimuli separated by different time intervals. In FIG. 4B, the initial pair of stimuli is separated by a very short interval, and subsequent pairs are separated by larger intervals. In an elevated [$K^+$] environment, the response will exhibit a two-peak ripple at a smaller interval than in a normal [$K^+$] environment. Processor 84 can detect the presence of the two-peak ripple using any signal processing technique, including techniques mentioned above.

Another distinction technique is to "sweep" through a range of frequencies, as illustrated by set of stimuli 148. In a normal [$K^+$] environment, the response 150 exhibits more rapid summation and reaches a sustained response in a shorter time. In contrast, the response 152 in an elevated [$K^+$] environment is slower to exhibit summation and sustained response. Processor 84 can detect the onset of rapid summation and sustained response any signal processing technique, including techniques mentioned above.

The signals depicted in FIGS. 4A and 4B are for purposes of illustration and the invention is not limited to signals of this type. Instead of measuring tension, as depicted in FIGS. 4A and 4B, sensor 80 could respond to muscle motion or muscle length, for example. In other embodiments, other signals may be measured in other tissue, which may be sensitive to [$K^+$] or other ion concentrations. For example, action potentials may be measured in nerve tissues.

As FIG. 4A shows, it may be more difficult to distinguish whether [$K^+$] is low or elevated when stimulations are applied at high frequencies. Further, the frequency at which a normal [$K^+$] environment can be distinguished from an elevated [$K^+$] environment may vary from patient to patient. Accordingly, a patient who has received IMD 12 may undergo one or more tests to calibrate muscle response to [$K^+$] or other tissue response to [$K^+$].

In other embodiments, the detection of different ion concentrations may be performed in a similar manner. However, delivered stimuli may be different depending on the tissue being stimulated and the ion concentration being detected.

Figure 5:
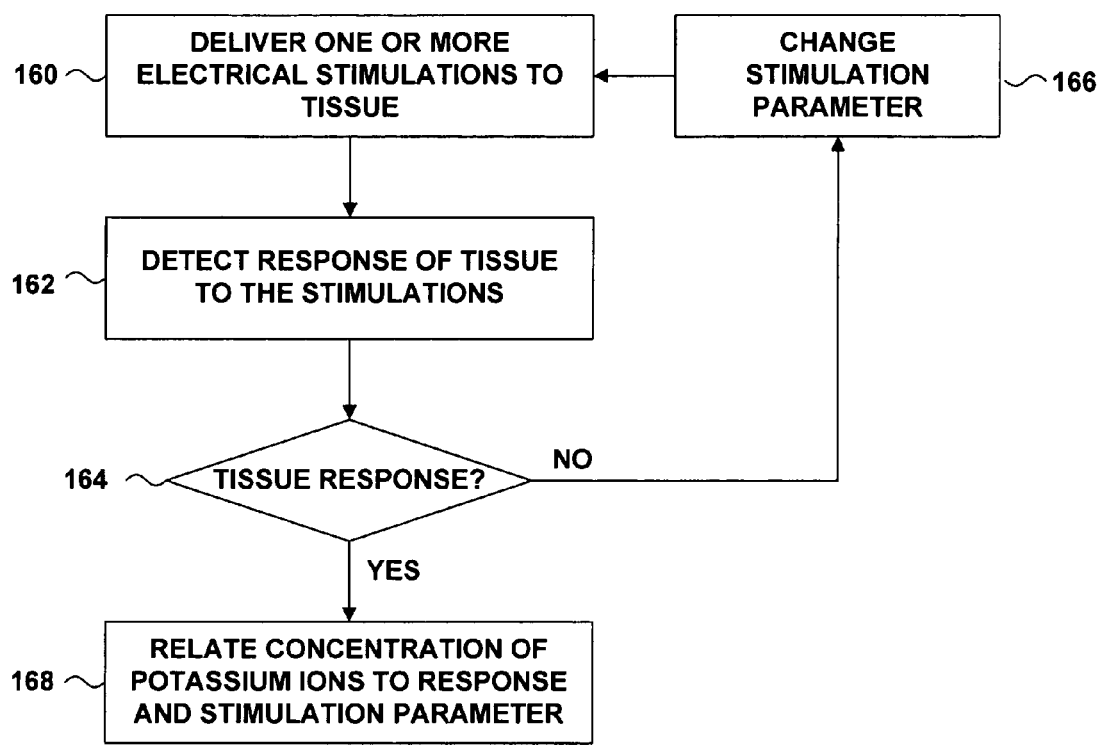
FIG. 5 is a flow diagram illustrating a technique for calibrating a medical device to determine a concentration of ions in extracellular fluid.

FIG. 5 illustrates an exemplary calibration procedure. Although FIG. 5 illustrates an example embodiment related to monitoring muscle tissue and [$K^+$], the illustrated technique may be applicable to calibration for monitoring of other tissues, such as nerve tissue, which may be sensitive to [$K^+$] and/or other ion concentrations.

In a laboratory setting, while conditions are suitable for stimulating the muscle and observing the response, IMD 12 delivers one or more electrical stimulations to the muscle of the patient via the electrodes (160). The stimulations may be delivered according to a particular parameter, such as a known frequency. For purposes of illustration, it is assumed that the stimulation parameter is a known frequency of stimulation, and that the initial known frequency is a low frequency. It is further assumed that the characteristic of interest is whether the muscle exhibits a sustained tissue response.

IMD 12 detects the response of the muscle to the stimulations (162) and performs signal analysis to determine whether stimulations at the known frequency produce a tissue response (164). If not, the frequency may be changed (166), e.g., increased, and the testing may be performed again (160). At some point, the patient will exhibit a rippled response, and at a higher frequency the patient will exhibit a sustained response.

At substantially the same time, the patient has his ECF [$K^+$] measured by conventional laboratory techniques. Data concerning [$K^+$] are then correlated to data pertaining to the patient's response to stimulation at one or more frequencies. In one embodiment, IMD 12 receives the data concerning measured [$K^+$], and processor 84 performs the correlation. In another embodiment, another processor performs the correlation, and the relationship is supplied to processor 84 via input/output element 88.

IMD 12 stores the relationship between a known [$K^+$] and the patient's response (168). In this way, a baseline measurement of [$K^+$] can be established for the patient. Future determinations of [$K^+$] can be measured against the baseline. If, at later time, the patient exhibits a sustained response at lower frequency, then [$K^+$] has declined in comparison to the baseline. Conversely, if the later patient exhibits a sustained response at higher frequency, then [$K^+$] has increased with respect to the baseline.

Although FIG. 5 illustrates calibration by observing sustained response, calibration may also be performed using other responses. Other responses can include, for example, the rate of relaxation following cessation of stimulation, the pulse width of a response, the occurrence of summation in the response, the amplitude of a response, or any combination thereof.

As part of the calibration, IMD 12 may deliver stimuli at different amplitudes. By iterative experimentation, IMD 12 can discover what amplitude of stimulation will produce a response. IMD 12 may be programmed to adjust the amplitude of stimulation as appropriate. Techniques to calibrate the IMD to detect other ions may be similar to the described technique to calibrate IMD 12 for [$K^+$].

Figure 6:
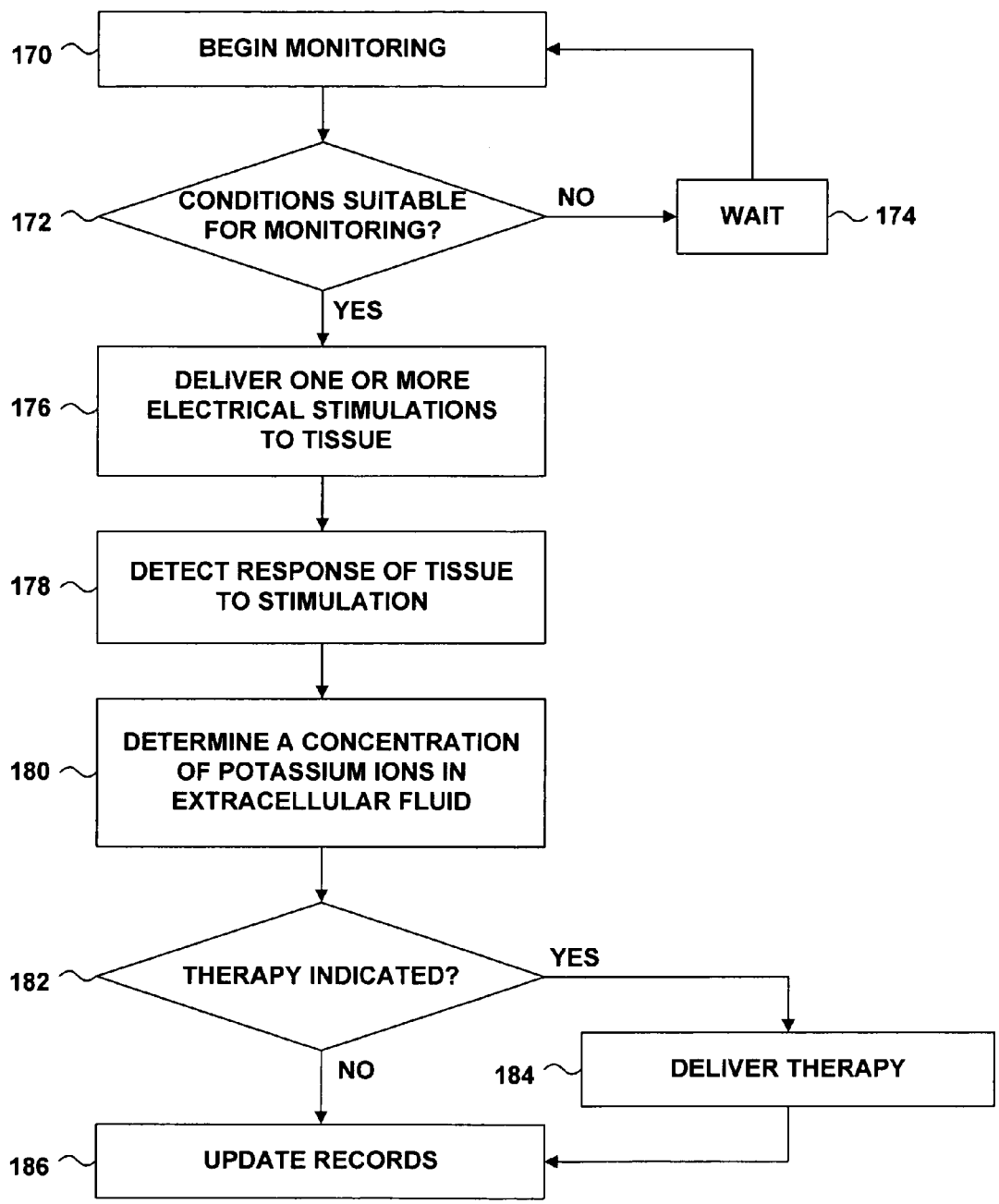
FIG. 6 is a flow diagram illustrating a technique for monitoring ion concentrations in extracellular fluid.

FIG. 6 is a flow diagram illustrating a technique for monitoring ECF potassium ion concentration and for delivering therapy in response to a determination of ECF potassium ion concentration. When, for example, processor 84 determines that it is time for a scheduled monitoring or when processor 84 detects a triggering event that can activate monitoring, processor 84 initiates the monitoring process (170). Before actually conducting the monitoring, however, processor 84 determines whether the conditions are suitable for monitoring (172). An illustrative situation in which conditions might not be suitable for monitoring is a situation in which the patient has a high level of physical activity. When a signal from an activity sensor indicates that the patient is physically active, it may be difficult to monitor [$K^+$] accurately. When processor 84 determines that conditions are not suitable for monitoring, processor 84 can defer monitoring to a later time (174).

IMD 12 delivers one or more electrical stimulations to the tissue of the patient (176). The stimulations may include a set of stimulations delivered at a known frequency or a set of stimulations that sweep through a range of frequencies. IMD 12 detects the response of the tissue to the stimulations (178). Although not depicted in FIG. 6, stimulations and detection (176, 178) may be repeated. For example, a later set of stimulations may be repeated at a known frequency that is different from an earlier set of stimulations.

On the basis of the detections, processor 84 determines a concentration of potassium ions in ECF of the patient (180). As noted above, this determination can include determining an absolute concentration, determining a relative concentration or determining a change in concentration, or any combination thereof.

On the basis of the determination of a concentration of potassium ions in ECF, processor 84 further determines whether action should be taken. In the example FIG. 6, the action in question is whether therapy is indicated (182). When therapy is indicated, processor 84 controls therapy element 90 to deliver therapy to the patient (184). The invention is not limited to instances in which IMD 12 takes action in the form of administration of therapy. Other kinds of action include transmitting a notification via input/output element 88 or changing how often IMD 12 monitors [$K^+$].

The results of the determination (180), and the delivery of therapy, if any, may be recorded in memory 86 (186). Among other purposes, data stored in memory are useful for monitoring the change in [$K^+$] over time and for documenting the response of the patient to therapy. Although described above with respect to [$K^+$], the techniques illustrated by FIG. 6 may additionally or alternative be used to monitor the concentration of ions other than potassium.

EXAMPLE 1

Figure 7:
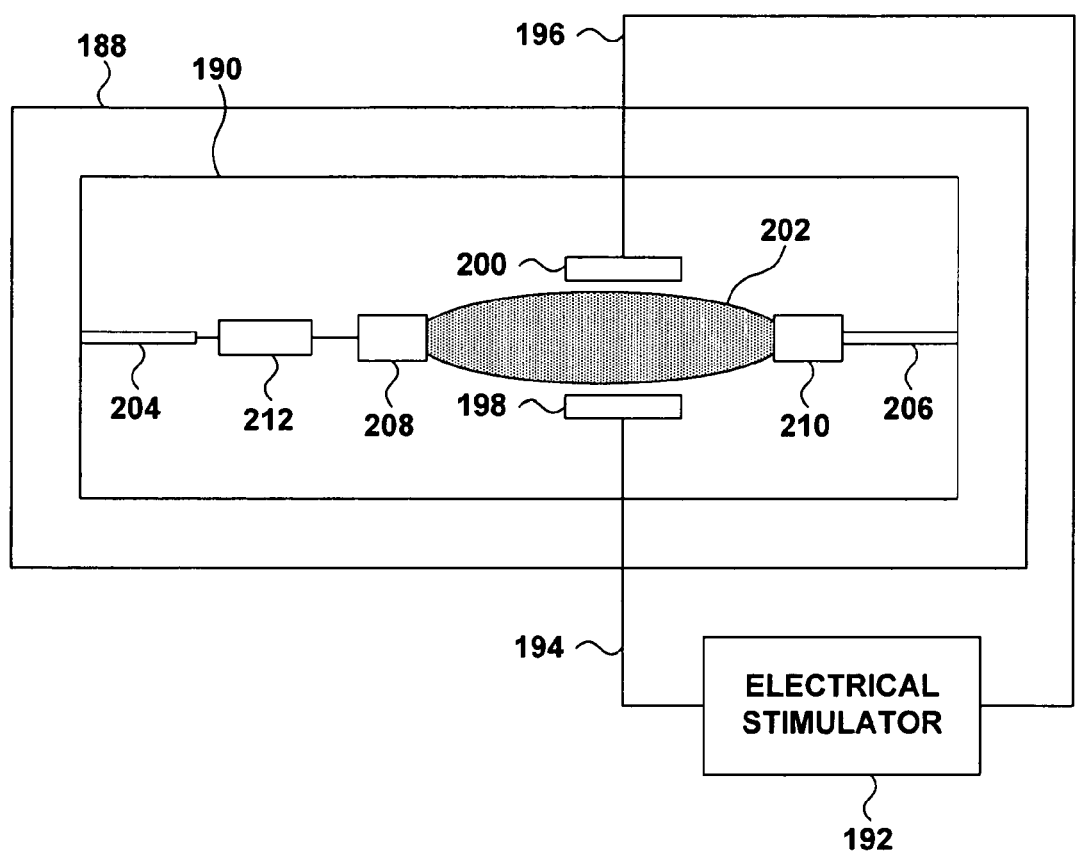
FIG. 7 is a schematic diagram of an experimental setup to test muscle contractions due to electrical stimuli.

FIG. 7 is a schematic diagram illustrating an experimental setup that was used to test muscle contractions due to electrical stimuli. As shown in FIG. 7, mouse skeletal muscle 202 was held between clamps 208 and 210 in a chamber 190. Clamp 210 was connected to a wall of chamber 190 by a support structure 206 while clamp 208 was connected to force transducer 212. Force transducer 212 was connected to support structure 204, which was attached to chamber 190. Chamber 190 was contained within bath 188. Electrical stimulator 192 provided electrical stimuli to muscle 202 through electrodes 198 and 200. Electrodes 198 and 200 were coupled to electrical stimulator 192 by wires 194 and 196, respectively.

Figure 8:
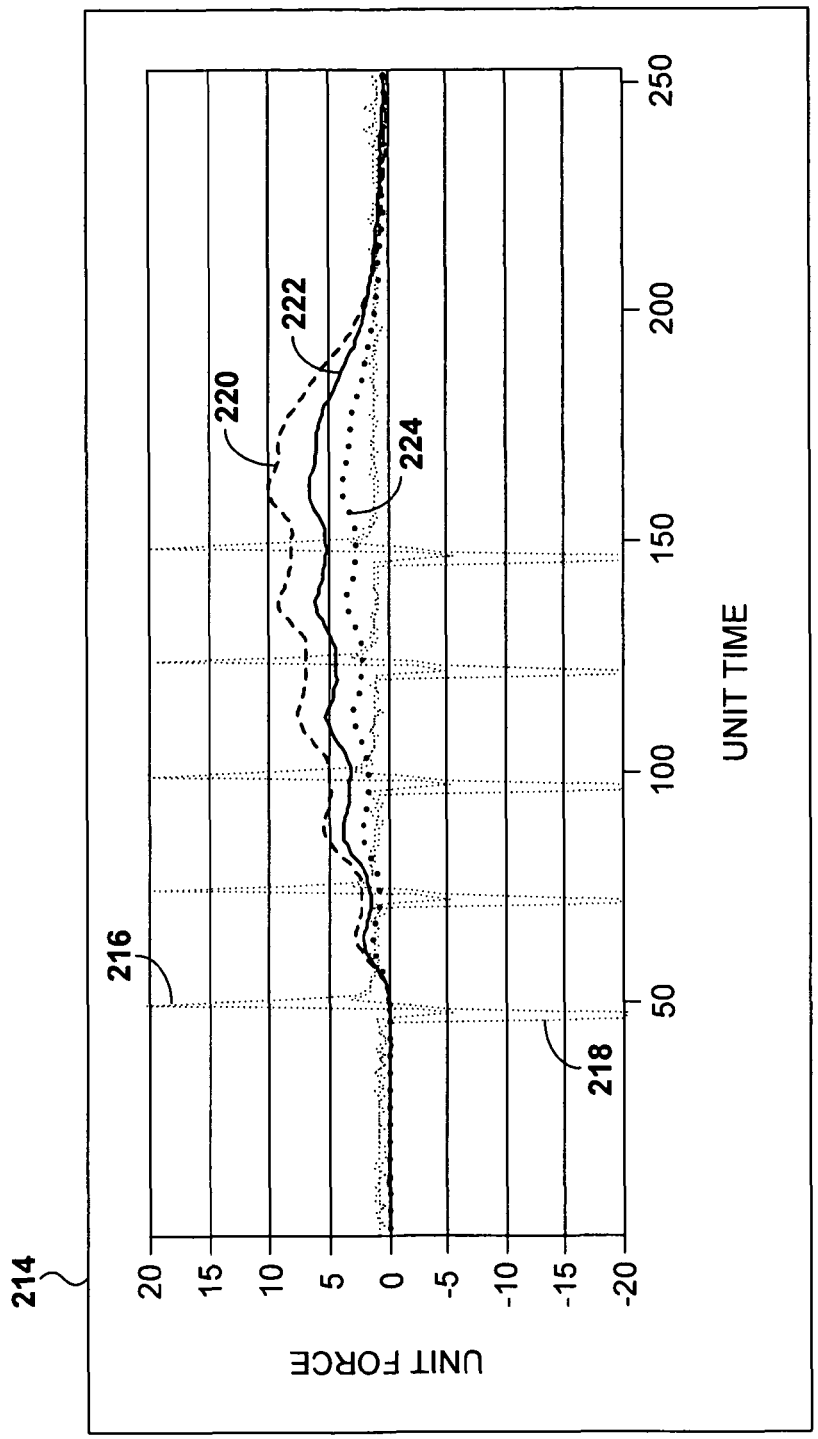
FIG. 8 is a graph of exemplary data showing muscle force in various solutions of potassium versus time.
Figure 9:
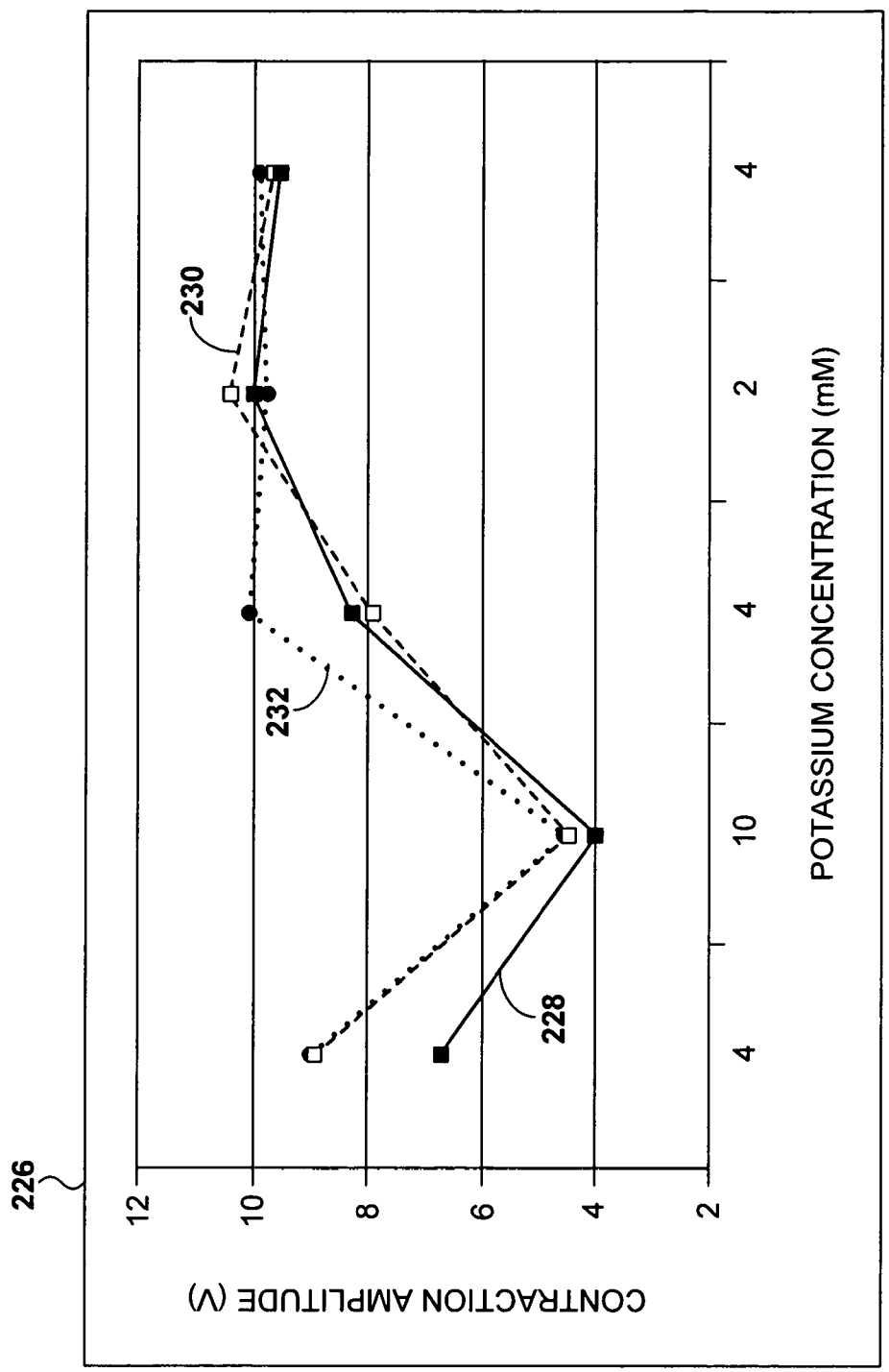
FIG. 9 is a graph of exemplary data showing contraction amplitude versus potassium concentration.

In the experiment described in FIGS. 7-9, bath 188 was set to 37 degrees Celsius, and chamber 190 was filled with potassium buffer that was controlled to provide varying concentrations of potassium ions to determine how muscle 202 contracts with electrical stimuli in the presence of differing potassium ion concentrations. Muscle 202 was an isolated mouse skeletal muscle. Force transducer 212 was a strain gauge. Biphasic electrical stimuli was delivered to muscle 202 via electrodes 198 and 200 in order to trigger isometric contractions in the muscle. A computing device monitors the measurements from force transducer 212 in real-time or offline. The experimental setup described in FIG. 7 may be varied to determine contraction forces from other tissues or using other devices.

FIG. 8 is a graph of experimental data showing muscle force in various solutions of potassium versus time. Graph 214 shows electrical stimuli 216 and 218 in conjunction with measured forces of muscle 202 of FIG. 7. Broken line 220 represents contractions when [$K^+$] equals 2 millimoles (mM), solid line 222 represents contractions when [$K^+$] equals 4 mM, and dotted line 224 represents contractions when [$K^+$] equals 10 mM. Contraction force was highest when [$K^+$] equaled 2 mM, which is a lower [$K^+$] than the normal potassium ion concentrations for a mouse. A medium level of force was generated with electrical stimuli when [$K^+$] equaled 4 mM, and the lowest levels of force was generated when [$K^+$] equaled 10 mM. Normal [$K^+$] of a mouse is approximately 4 mM.

In the experiment, a burst electrical stimulation consisting of 5 pulses with a frequency of 50 Hz were applied to muscle 202. Pulses were biphasic with anodic and cathodic pulse durations of 1 millisecond (ms), and 18 ms of pause between each pulse.

FIG. 9 is a graph of experimental data showing contraction amplitude versus potassium concentration. Graph 226 displays contraction amplitudes in Volts according to three different electrical stimuli frequencies. Volts may be translated into force measurements by a calibration procedure. Solid line 228 and included closed boxes are representative of 50 Hz stimulation, broken line 230 and included open boxes are representative of 100 Hz stimulation, and dotted line 232 and included closed circles are representative of 150 Hz stimulation.

The [$K^+$] was varied in the sequence of 4 mM, 10 mM, 4 mM, 2 mM, and 4 mM. The results showed that the amplitude of the force generated by muscle 202 may be determined by the [$K^+$] when the stimulation frequency 50 Hz and 100 Hz. In addition, stimulation at 150 Hz may also be used to determine [$K^+$] in skeletal muscle, but was less sensitive to [$K^+$] than the other frequencies tested. Other frequencies not tested in the experiment of FIGS. 7-9 may also be useful for electrical stimulation.

In some embodiments, other tissues may be tested and may respond similarly as the mouse skeletal muscle. Other frequencies and [$K^+$] may also be tested, while the exemplary conditions provided herein are only a small sample of [$K^+$] that may be detected with electrical stimulation.

The invention may produce one of more advantages. In comparison with conventional implantable ion sensors such as electrochemistry-based ion sensors or optically based sensors, the invention supports long-term implantation. Conventional ion sensors have proven to be unstable over extended periods. Some sensors require a periodic replacement of a sensing element, and other sensors lose sensitivity when the body naturally encapsulates the implanted elements. Some sensors also can be rejected by the body of the patient.

IMDs such as those described above, however, have proven to be well tolerated in the long term. Rejection rates are low. Further, the IMD can respond to encapsulation by increasing the voltage of stimulations to provoke a response.

The stimulations need not be painful. In practice, the patient may very likely experience a tingle. The tingle may be uncomfortable, but it would probably not be painful as long as stimulations are adjusted to a voltage that provokes a response and is not excessive. Further, as discussed above, the stimulations may be therapeutic stimulation of, for example, cardiac muscle or nervous tissue, that would have otherwise been delivered to the patient whether or not [$K^+$] was monitored. There may further be an element of convenience to the patient, as the patient may reduce the number of tests that rely upon blood samples.

IMDs such as those described above can be implanted using conventional, well-established surgical techniques. In the case of an IMD that delivers pacing or other heart therapies, an electrode configured to deliver an electrical stimulation to a tissue may be deployed as part of conventional device implantation technique, with little or no additional incision or trauma to the patient. Many patients experiencing heart failure may benefit from the implantation of an IMD that combines pacing therapies and potassium monitoring capability.

In addition, the invention supports embodiments that include one or more external elements, which may offer further advantages. A patient may receive the embodiment depicted in FIG. 1F, for example, without surgery. An external electrode element, such as that depicted in FIG. 1F, may be deployed at several sites on the body of the patient without surgery. An external electrode element may also be readily redeployed from one site to another.

Various embodiments of the invention have been described, but the invention is not limited to these particular embodiments. Although the invention has been depicted in the context of a pacemaker having one or more leads configured to deliver pacing stimuli to a heart, the invention can also be implemented in conjunction with other implantable and external devices. The invention can be implemented with a neurostimulator that includes a lead configured to deliver a pacing stimulation to a nerve, or a drug pump that includes a pump configured to deliver a drug to the patient from a reservoir. The invention may also be implemented as a standalone ion imbalance detector.

The invention may be embodied in a transitory or non-transitory computer-readable medium with instructions that cause a programmable processor to carry out the techniques described above. A "computer-readable medium" includes but is not limited to read-only memory, Flash memory, EPROM and a magnetic or optical storage medium. A non-transitory computer readable medium includes all computer readable media except for a transitory, propagating signal. The medium may comprise instructions for causing a programmable processor to control a pulse generator to deliver an electrical stimulation to a muscle in a patient, for example, or receive from a sensor a signal indicative of a response of the tissue to the electrical stimulations.

Further, although described above primarily with reference to skeletal muscle tissue and potassium ion concentrations, the techniques of the invention may be applied to monitoring the response of any tissue to the concentration of any one or more ions. Example tissues include skeletal, cardiac or smooth muscle, as well and nerve or dermal tissues. Example ions include potassium, sodium, chloride, calcium, or magnesium ions, as well as drugs that become ions in the blood or ECF, small molecules, or endogenously charged molecules. Examples of drugs that may be monitored as ions in the ECF include lodipine, felodipine, furosemide, bumetanide, isosorbide dinitrate, dantrolene, digoxin, digitalis, carisoprodol, chlorphenesin, calcium channel blockers, diuretics, vasodilators, muscle relaxants and calcium blocker for malignant hyperthermia. These and other embodiments are within the scope of the following claims.

What is claimed is:

1. A method comprising:
   delivering an electrical stimulation to a tissue in a patient using an electrode;
   detecting a response of the tissue to the electrical stimulation using a sensor; wherein the response is any one or more selected from the group consisting of a sustained contraction of the tissue, a rippled contraction of the tissue, a rate of relaxation of the tissue, a pulse width of the response, an occurrence of summation in the response, an amplitude of the response, muscle tension, muscle motion or muscle length, a decline of muscle tension following cessation of the stimulation, and a fall time of muscle tension following cessation of the stimulation; and
   storing a relationship between a concentration of ions in extracellular fluid of the patient and the response in a non-transitory, computer readable medium.

2. The method of claim 1, wherein the ions are at least one of potassium, sodium, chloride, calcium, bicarbonate, or magnesium ions.

3. The method of claim 1, wherein the electrical stimulation is delivered to any of cardiac muscle, skeletal muscle, smooth muscle, nerve tissue, or skin of the patient.

4. The method of claim 1, wherein the electrical stimulation is a first electrical stimulation and the response is a first response, the method further comprising
   delivering a second electrical stimulation to the tissue;
   detecting a second response of the tissue to the second electrical stimulation; and
   determining a concentration of ions in the extracellular fluid of the patient as a function of the first and second responses.

5. The method of claim 4, wherein determining the concentration of ions in the extracellular fluid of the patient comprises determining a change in concentration of ions in the extracellular fluid over time.

6. The method of claim 4, wherein the first electrical stimulation and second electrical stimulation each comprise two stimulations; wherein the time between the two stimulations of the first electrical stimulation is different from the time between the two stimulations of the second electrical stimulation.

7. The method of claim 4, wherein the frequency of the first electrical stimulation is different from the frequency of the second electrical stimulation.

8. The method of claim 1, further comprising determining the absolute concentration of ions in the extracellular fluid.

9. The method of claim 1, further comprising determining the activity status of the patient; wherein the electrical stimulation is delivered when the activity status of the patient is inactive.

10. The method of claim 1, wherein storing a relationship between a concentration of ions in extracellular fluid of the patient and the response comprises storing a relationship between a concentration of 2 or more different ions in extracellular fluid of the patient and the response.

11. The method of claim 10, wherein the relationship between the concentration of 2 or more different ions in extracellular fluid of the patient and the response comprises a ratio of the 2 or more different ions in extracellular fluid.

12. The method of claim 1, wherein the response is any one of muscle tension, muscle motion or muscle length.

13. The method of claim 1 wherein the response is the decline of muscle tension following cessation of the stimulation.

14. The method of claim 1 wherein the response is the fall time of muscle tension following cessation of the stimulation.

15. A system, comprising
   a control unit configured to control a pulse generator to deliver an electrical stimulation to a tissue in a patient; and
   a processor configured to receive from a sensor a signal indicative of a response of the tissue to the electrical stimulations and store a relationship in a non-transitory, computer readable medium between a concentration of ions in extracellular fluid of the patient and the response; wherein the response is any one or more selected from the group consisting of a sustained contraction of the tissue, a rippled contraction of the tissue, a rate of relaxation of the tissue, a pulse width of the response, an occurrence of summation in the response, an amplitude of the response, muscle tension, muscle motion or muscle length, a decline of muscle tension following cessation of the stimulation, and a fall time of muscle tension following cessation of the stimulation.

16. The system of claim 15, wherein the ions are at least one of potassium, sodium, chloride, calcium, or magnesium ions.

17. The system of claim 15, wherein the processor is further configured to receive data concerning a measured concentration of ions in the extracellular fluid; and correlate the measured concentration with the response.

18. The system of claim 15, wherein the signal indicative of a response of the tissue to the electrical stimulations is a radio frequency signal or a wire transmitted signal.

19. The system of claim 15, wherein the processor is configured to transmit the relationship between the concentration of ions in extracellular fluid of the patient and the response to an external computing device.

\* \* \* \* \*